US005788215A

United States Patent [19]
Ryan

[11] Patent Number: 5,788,215
[45] Date of Patent: Aug. 4, 1998

[54] MEDICAL INTRAVENOUS ADMINISTRATION LINE CONNECTORS HAVING A LUER OR PRESSURE ACTIVATED VALVE

[75] Inventor: Dana Wm. Ryan, Woodward, Okla.

[73] Assignee: Rymed Technologies, Woodward, Okla.

[21] Appl. No.: 581,057

[22] Filed: Dec. 29, 1995

[51] Int. Cl.$^6$ ...................................................... A61M 5/00
[52] U.S. Cl. ...................... 251/149.6; 604/167; 604/256
[58] Field of Search .............................. 251/149.1, 149.6, 251/149.8; 604/247, 256, 249, 167

[56] References Cited

U.S. PATENT DOCUMENTS

| | | |
|---|---|---|
| 3,192,949 | 7/1965 | De See . |
| 3,799,171 | 3/1974 | Patel . |
| 3,806,086 | 4/1974 | Cloyd . |
| 4,349,021 | 9/1982 | Raible ............................ 604/167 X |
| 4,617,015 | 10/1986 | Foltz . |
| 4,723,550 | 2/1988 | Bales et al. ..................... 604/256 X |
| 4,776,369 | 10/1988 | Lardner et al. . |
| 4,908,018 | 3/1990 | Thomsen . |
| 4,915,687 | 4/1990 | Sivert . |
| 5,024,657 | 6/1991 | Needham et al. . |
| 5,085,645 | 2/1992 | Purdy et al. ..................... 604/256 X |
| 5,116,021 | 5/1992 | Faust et al. . |
| 5,163,922 | 11/1992 | McElveen, Jr. . |
| 5,181,913 | 1/1993 | Erlich . |
| 5,181,921 | 1/1993 | Makita et al. . |
| 5,195,967 | 3/1993 | Nakao et al. . |
| 5,201,725 | 4/1993 | Kling . |
| 5,203,775 | 4/1993 | Frank et al. . |
| 5,215,538 | 6/1993 | Larkin . |
| 5,217,434 | 6/1993 | Arney . |
| 5,242,393 | 9/1993 | Brimhall et al. . |
| 5,242,423 | 9/1993 | Goodsir et al. . |
| 5,250,028 | 10/1993 | Theeuwes et al. . |
| 5,250,034 | 10/1993 | Appling et al. . |
| 5,259,839 | 11/1993 | Burns . |
| 5,269,771 | 12/1993 | Thomas et al. . |
| 5,280,876 | 1/1994 | Atkins . |
| 5,284,475 | 2/1994 | Mackal . |
| 5,290,263 | 3/1994 | Wigness et al. . |
| 5,300,033 | 4/1994 | Miller . |
| 5,300,044 | 4/1994 | Classey et al. . |
| 5,308,334 | 5/1994 | Sancoff . |
| 5,322,518 | 6/1994 | Schneider et al. . |
| 5,330,435 | 7/1994 | Vaillancourt . |
| 5,334,170 | 8/1994 | Moroski . |
| 5,336,174 | 8/1994 | Daoud et al. . |
| 5,336,192 | 8/1994 | Palestrant . |
| 5,338,313 | 8/1994 | Mollenauer et al. . |
| 5,353,837 | 10/1994 | Faust . |
| 5,356,375 | 10/1994 | Higley . |
| 5,360,413 | 11/1994 | Leason et al. . |

(List continued on next page.)

*Primary Examiner*—Kevin Lee
*Attorney, Agent, or Firm*—David P. Gordon; Thomas A. Gallagher

[57] ABSTRACT

Medical intravenous administration connectors include a first coupling member having a female luer, a valve member having a substantially rigid stem and a substantially resilient body with a sealing surface, and a second coupling member having a fluid coupling extending from one end and an internal valve member support. The coupling members are structured to couple to each other with the valve member being biased to a closed position. When assembled, the valve stem extends into the female luer, and the valve body biases the sealing surface against an annular ring in the first coupling member thereby blocking fluid communication. Preferably, vanes are provided in the second coupling member on which the resilient body of the valve sits, with the vanes acting as a centering mechanism for the valve. The valve may be opened for fluid flow through the assembly by coupling a male luer to the female luer of the assembly, or by pressure actuation. Several valve members are disclosed and several structures for mating the first and second coupling members are disclosed. Y-injection sites and intravenous manifolds utilizing the valve arrangement and coupling members of the invention are also disclosed. All embodiments are easy to prime, limit priming volume, and are arranged without dead-spaces in which blood can be trapped.

35 Claims, 12 Drawing Sheets

U.S. PATENT DOCUMENTS

| | | |
|---|---|---|
| 5,364,371 | 11/1994 | Kamen . |
| 5,370,624 | 12/1994 | Edwards et al. . |
| 5,390,898 | 2/1995 | Smedley et al. . |
| 5,391,150 | 2/1995 | Richmond . |
| 5,399,171 | 3/1995 | Bowman et al. . |
| 5,401,255 | 3/1995 | Sutherland et al. . |
| 5,405,323 | 4/1995 | Rogers et al. . |
| 5,465,938 | 11/1995 | Werge et al. ......................... 251/149.1 |
| 5,535,771 | 7/1996 | Purdy et al. ......................... 604/256 X |
| 5,578,059 | 11/1996 | Patzer ................................. 604/256 X |

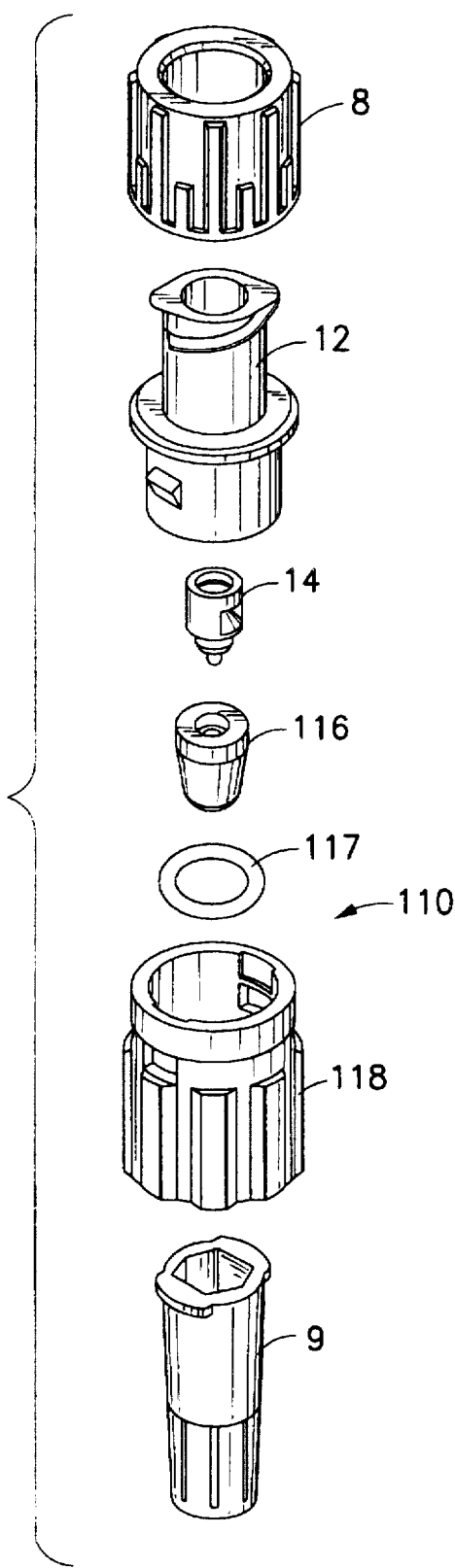
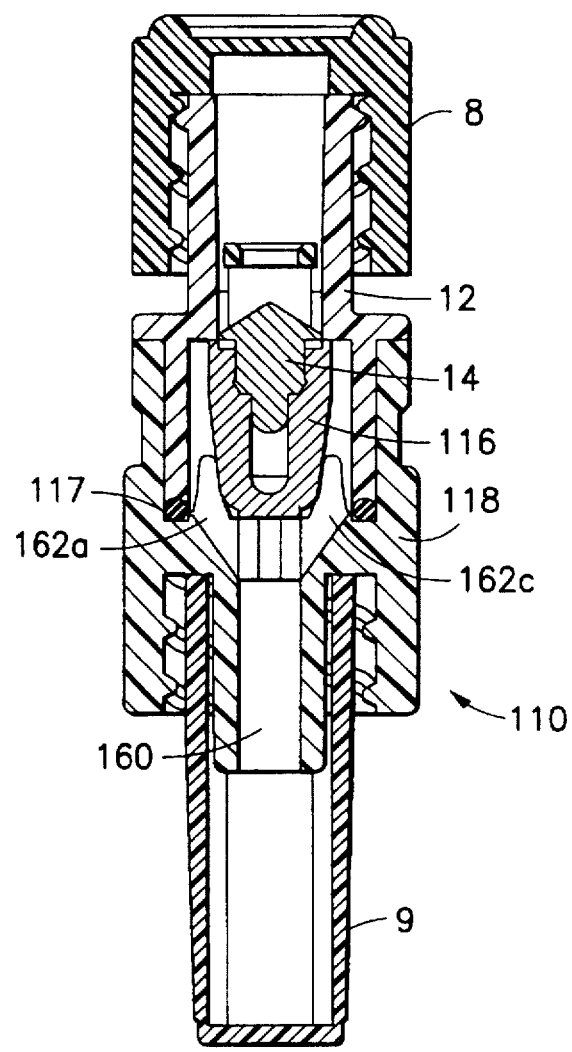
FIG. 7
FIG. 8

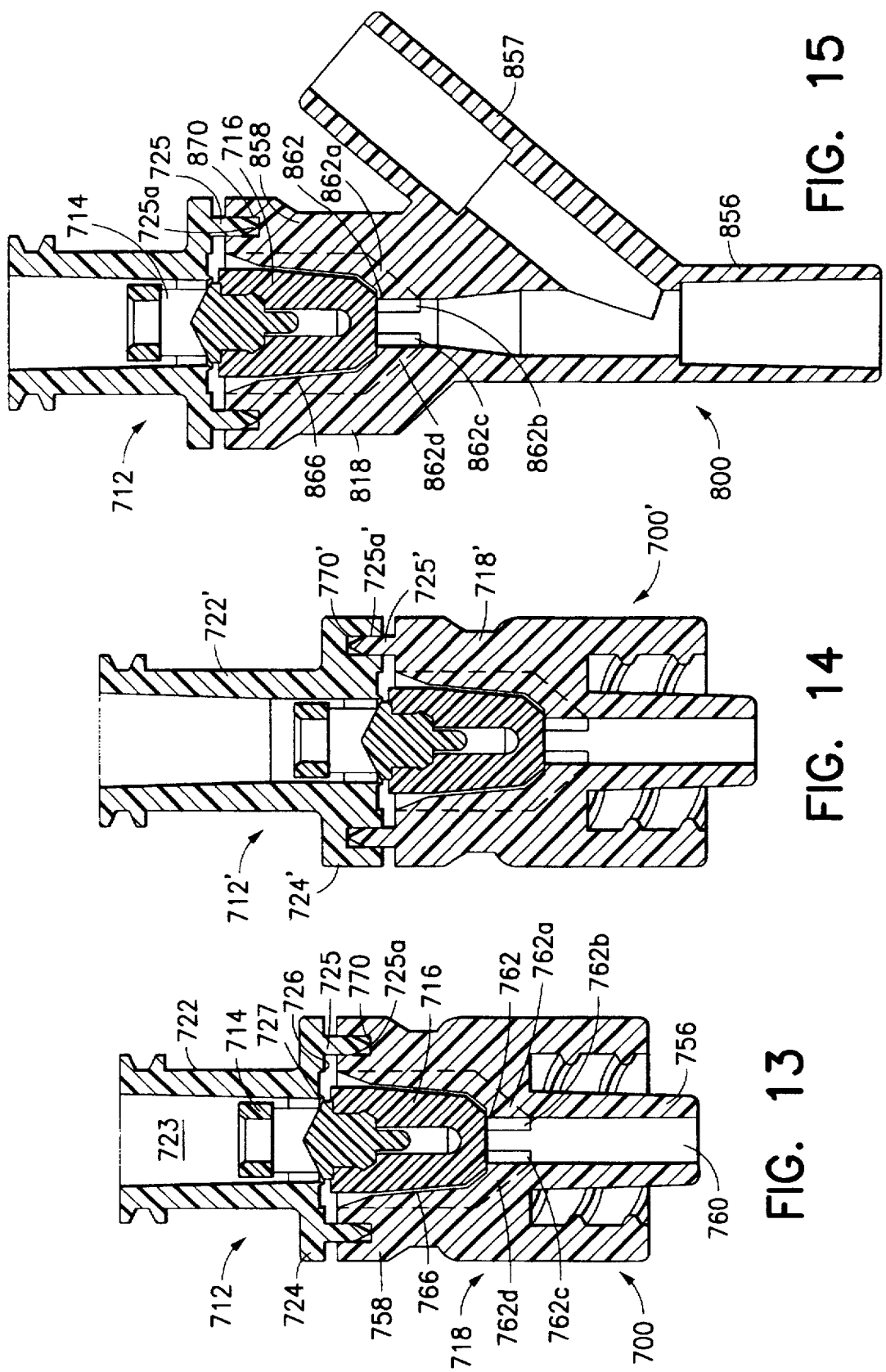

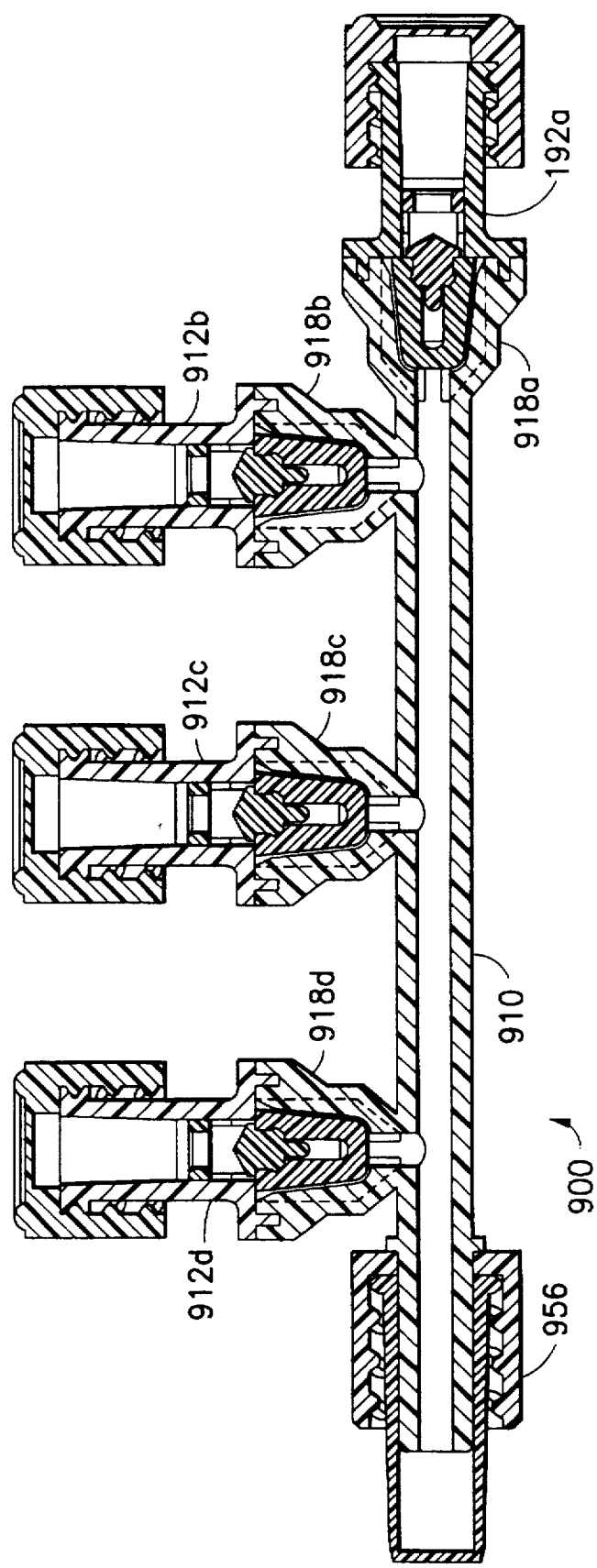

MEDICAL INTRAVENOUS ADMINISTRATION LINE CONNECTORS HAVING A LUER OR PRESSURE ACTIVATED VALVE

BACKGROUND OF THE INVENTION

1. Field of the Invention

This invention relates to medical IV administration line connectors. More particularly, this invention relates to needleless injection ports for the safe infusion and/or aspiration of fluids in intravenous and blood administration therapy.

2. State of the Art

Intravenous therapy has a long history of use in supplying patients with pharmaceuticals, liquid nourishment, or blood products. Prior art FIGS. 17 through 20 show that the current or conventional way introducing parenteral liquid solutions and/or blood and blood products into a patient is by the conventional gravity feeding system 1000. The feeding system 1000 includes a container 1002 that is either a bottle or bag for the parenteral solution, a tube 1004 extending from the bottle or bag and connected to a Y-injection site 1006 (piggyback or secondary Y-injection site), and a tube 1008 from the Y-injection site 1006 to a needle or catheter 1010 which is inserted into a vein in the arm 1012 of the patient. The vein-access needle or catheter is taped to the patient with adhesive tape 1014 so that the chance of a detachment and disconnect from the vein is minimized.

Supplemental intravenous therapy from a piggyback or secondary bottle or bag 1016 is introduced through the Y-injection site 1006 into the primary intravenous administration set 1000. As seen best in FIG. 19, the Y-injection site 1006 which is integrated into the primary intravenous administration set 1000 consists of two tubular conduits 1006a, 1006b which merge into a third tubular conduit 1006c. The tubing 1002 from the bottle or bag of parental solution of the primary intravenous administration set 1000 is attached into the inlet port 1006a of the Y-injection site. In similar fashion, the tube 1008 is attached into the exit port 1006c of the Y-injection site. A sealed entry port segment 1007 of the Y-injection site 1006 is provided by the extension conduit 1006b which has a standard, self-sealing latex rubber septum 1007a at its inlet port to seal this port from leakage. Consequently, it is difficult for pathogens to enter the Y-injection site 1006 via the septum port 1007 because of the seal 1007a. This self-sealing septum 1007a is of a conventional design and includes coaxial annular aprons which fit over the conduit wall and grip the external and internal wall surfaces to hold the septum securely to the conduit 1006b. Typically, a plastic shrink-band (not shown) is shrunk on the outer wall of the septum 1007a to securely connect it to the extension conduit 1006b.

The supplemental intravenous solution is introduced into the primary intravenous administration set 1000 through the Y-injection site 1006 by way of a primed piggyback or secondary intravenous set 1016. The piggyback or secondary intravenous set 1016 has a hollow-bore needle 1018 attached to its distal end, which in turn is inserted through the self-sealing septum 1007a of the Y-injection site 1006 and into the extension conduit 1006b. This needle 1018 is connected to a tube 1020 which is connected to a dripchamber (not shown) of the piggyback or secondary intravenous set 1016. A roller clamp 1004a, 1020a is typically used on both the primary and piggyback/secondary intravenous sets to control liquid flow rates into the patient.

There are several problems associated with the standard techniques employed for intravenous therapy. If the piggyback needle 1018 is not securely taped to the Y-injection site 1006 and the primary intravenous administration set tubing 1002, 1008, patients can move their arms, or roll over in bed accidentally pulling the needle 1018 completely out of the septum 1007a on the Y-injection site 1006. If this occurs, the self-sealing latex septum 1007a will close off automatically and not allow liquid or contamination to enter the primary intravenous administration set 1000. The primary intravenous solution in the bottle or bag 1002 will continue to flow into the patient, but, the necessary supplemental pharmaceutical solution from the piggyback or secondary bottle or bag 1016 will no longer flow into the patient via the Y-injection site 1006. The consequences to the patient for this situation can lead to serious complications and even death if the condition is not noticed by a clinician immediately. Even if the clinician notices the detachment of the needle 1018 from the Y-injection site septum 1007a immediately, the needle 1018 is now contaminated with pathogens and should never be introduced back into the septum 1007a. A new sterile, piggyback/secondary intravenous set must be opened, primed, and a new hollow-bore needle reinserted back into the septum on the Y-injection site. Additionally, whether the needle 1018 is accidentally detached, or, the clinician removes the needle 1018 from the Y-injection site septum once the supplemental pharmaceutical therapy is completed for the patient, the exposed needle 1018 is contaminated with pathogens and must be safely disposed by the clinician without accidentally sticking themselves.

To avoid accidental removal, the needle of the piggyback or secondary intravenous set may be taped to the Y-injection site and extension port. When this occurs, the needle may be secured from detachment, but the needle cannot be easily and safely removed by the clinician when the supplemental pharmaceutical therapy is completed, thereby creating a higher incidence for an accidental needle stick injury. Also, because clinicians hold the Y-injection site with one hand while the other hand is used to insert the needle into the Y-injection site septum, the clinicians may accidentally stick the needle directly into their hands holding the Y-injection site, or stick the needle completely through the Y-injection site wall into their hands.

The above description and problems associated with conventional continuous and supplemental intravenous therapy through a Y-injection site is similar to the problems associated with intermittent intravenous therapy using a "Heparin Lock" injection port 1030 (FIGS. 18 and 20). A heparin lock injection port 1030 is either connected directly to the vein-access device 1010, or attached to a short catheter extension tubing set 1032 typically with microbore tubing which is attached to the vein-access device as shown in FIG. 18. The heparin lock has a self-sealing septum port 1034 which is similar to the septum port 1007 described above. A conventional intermittent intravenous therapy could utilize a short-term primary intravenous administration set 1016 with a hollow-bore needle 1018 attached to the distal end of a tube 1020. The needle would be inserted to the self-sealing septum found on standard heparin lock injection port 1030. Another means of introducing supplemental intermittent pharmaceuticals to a patient is to perform an intravenous push utilizing a syringe with a hollow-bore needle attached. The drug is pushed into the patient through the heparin lock injection port 1030. Once dispensed, the syringe/contaminated needle is removed from the self-sealing septum 1034 on the heparin lock injection port 1030.

As set out above, the common medical techniques for delivering supplemental liquid fluids to the patient necessitates the use of a hollow-bore needle. The needle is either attached to a secondary intravenous set or a syringe, and is inserted through the self-sealing rubber stopper on the heparin lock injection port or the Y-injection port that is integrated into the primary intravenous administration set. Typically, the needle is secured to the injection port only with tape. The needle can detach from the injection port resulting in a serious or fatal interruption of the flow of the intravenous solutions to the patient. Moreover, the exposed needle can easily be contaminated by contact with non-sterile objects. Good aseptic technique must be practiced by the healthcare professional in order to ensure that the sterile needle does not become contaminated and cause a nosocomial infection to the patient.

Since the discovery of the HIV virus that causes AIDS in the mid-1980's, a major concern among healthcare workers practicing the standard methods of delivering intravenous therapy is accidental needle sticks with a contaminated needle. When a needle is removed from an injection port, it may be contaminated with the patient's blood. The contaminated needle must be carefully disposed in a sharps container. While handling the needle during removal and disposal, clinicians may, and often do, inadvertently stick themselves. Among all of the needled medical devices used in healthcare facilities, contaminated intravenous needles are responsible for the most accidental needlestick injuries. When a needlestick injury occurs, the clinician must stop work and have a blood test performed. Since a needlestick injury can result in fatal disease, the injured clinician will also experience tremendous emotional trauma.

Accidental needlestick injury is one of the leading causes of disease among healthcare workers throughout the world. With over twenty different infections that can be transmitted via contaminated needles, most notably Hepatitis B, C, and HIV viruses, the Center for Disease Control (CDC) and OSHA have enacted stringent regulations and guidelines which now require protocols and engineering controls to eliminate or at least minimize needlestick injuries.

There is a wealth of prior art concerned with the problem of accidental needlesticks. For example, U.S. Pat. No. 5,199,947 to Lopez discloses an influent line piggyback connector which includes a male member and a female member. The male member is a piggyback connector with a self-sealing rubber entry port (septum) at its end. The female member is a plastic tube which safely houses a needle and is provided with a locking lever. When the male and female members are engaged, the needle centrally pierces the septum of the port upon engagement of the members and the locking lever provides a "click" sound when it locks the members together. While the Lopez device has certain advantages in the prevention of needlestick injuries, it still employs a steel needle, and is relatively large and bulky. It requires numerous component parts for the assembly, and the male and female connectors can only be used with each other. In order for a healthcare facility to use the product, these special connectors and injection ports have to be attached to the standard intravenous sets and syringes. Also, after numerous penetrations by the large hollow-bore needle, the rubber septum is prone to leakage and possible contamination.

My prior U.S. Pat. No. 5,139,483 improved on the Lopez design by reducing the number of component parts for the assembly, as well as by reducing the overall size and weight of the product. My intravenous quick connect and disconnect device includes suitably molded single piece male and female connectors. The male connector has a male luer-lock on one end, one or more outwardly extending bayonet knobs on a middle portion and a reduced diameter second end which terminates in a resilient self-sealing septum. The female connector has a female luer-lock on one end and a receiving cylinder with a bayonet receiving cutout on the other, the luer-lock and the cylinder being separated by a wall. A hollow needle is insert-molded in the wall and extends into the receiving cylinder. The male and female connectors are mated by sliding the reduced diameter second end of the male connector into the receiving cylinder of the female connector, with the bayonet receiving cutouts of the female connector serving as a track for the bayonet knobs of the male connector. The connectors are locked into place by bringing the male connector as far forward as possible, and then rotating the male connector such that knobs move past the restriction in the cutout and a "click" lock into place. The bayonet lock design secures the two members together, eliminating the need for tape and reducing the chance of a disconnect. Although this arrangement overcomes many of the disadvantages of the prior art, it still has its deficiencies. The invention prevents needlestick injuries, but it still employs a steel needle, and requires additional special connectors and injection ports in order to utilize the product. After numerous penetrations by the large hollow-bore needle, the rubber septum becomes prone to leakage. Also, while products made according to the invention may carry needles of different gauges, there is no easy way to identify the gauge of needle. In addition, the female connector exposes the bayonet cutouts on its outer surface and the male connector exposes the bayonet knobs on its outer surface. The outwardly exposed cutouts and knobs present rough surfaces which, during attachment, present a possibility of catching or tearing the vinyl or latex gloves worn by the clinician.

My prior U.S. Pat. No. 5,292,308 solves some of the aforementioned disadvantages by providing a suitably molded single-piece male connector and a two-piece female connector. The male connector has a male luer on one end, one or more inwardly extending bayonet recesses on the surface of a middle section and a reduced diameter second end enclosing a resilient self-sealing septum. The female connector has a luer on one end and a two part receiving cylinder on the other with inwardly extending bayonet knobs. The luer and the first part of the cylinder are separated by a wall through which a hollow-bore needle extends. The connectors are mated by sliding the second end of the male connector into the receiving cylinder of the female connector with the knobs of the female connector being guided by the recesses of the male connector. The connectors are locked into place by bringing them together, and then rotating them such that knobs move past restrictions in the recesses and lock into place. The parts of the female connector are joined together by sonic welding or solvent bonding which is enhanced by providing one with a reduced inner diameter end and the other with a reduced outer diameter end so that the parts join in a male/female relationship. The ends of the two parts are preferably faceted to prevent relative rotation of the joined parts. The second part of the cylinder is advantageously color-coded to identify the type or gauge of needle being carried. The outside cylindrical surfaces of both the male and female connectors (both before and after mating) are smooth with no projections that can catch or tear the clinician's gloves.

In using the male and female connectors, the distal end of an intravenous administration set is inserted into the female luer side of the female connector. The male connector with the resilient self-sealing septum is connected directly to a vein-access device such as a peripheral intravenous catheter.

central venous catheter, or a scalp-vein needle set. Once the vein-access device is in place on the patient and the male connectors is coupled to it, the female connector which has been coupled to the IV administration set may be coupled to the male connector as described above. The needle in the female connector pierces the resilient septum of the male connector which permits the flow of liquid through the septum via the hollow-bore needle. The connectors are securely locked into place by the bayonet knobs and recesses which "click" lock into place. Quick release is obtained by rotating the male and/or female connector in the opposite direction and pulling the male connector straight out relative to the female connector. When the male and female connectors are separated, the needle in the female connector is withdrawn from the self-sealing resilient septum held in the reduced diameter second end of the male connector. The contaminated needle is safely shielded within the cylinder of the female connector.

Despite all of the safety features in the prior art described above, all the connector systems still require a piercing needle, a septum, and additional special components in order to deploy the systems. It is currently appreciated that a completely "needleless" injection port that is activated by standard male-luers would offer substantial advantages.

Needleless valves are not unknown in the art of intravenous administration. U.S. Pat. No. 3,831,629 to Mackal discloses a check valve primarily suited for applications in which it is subjected to low fluid pressures. The two-piece check valve has a cylindrical valve body which has a stepped throughbore. A cylindrical valve element is mounted within the valve body. The valve element includes a valve stem and art integral elastomeric rear end portion of larger diameter than the stem and defining a sealing shoulder therebetween. The valve element is mounted inside the valve body so that its stem extends into the reduced diameter front portion of the throughbore and its elastomeric rear end resides in the larger diameter rear portion of the throughbore. The rear end of the valve body is radially crimped so that the valve element is held in axial compression with the shoulder of the valve element sealing the stepped throughbore of the valve body. When a nozzle is inserted into the front end of the valve body, it pushes on the valve stem and moves the shoulder rearward to open the valve. The resiliency of the valve element causes the valve to reseal when the nozzle is removed. While the check valve disclosed by Mackal is relatively simple and easy to assemble, it is not readily adapted for use in an intravenous and/or blood administration applications. The valve element is made of a one-piece elastomeric material, with a very small fluid channel on the valve stem. With the numerous variations of male-luer connectors throughout the world, the Mackal check valve has a major disadvantage. With some particular male-luer connectors, fluid flow rates will be significantly reduced. Intravenous therapy applications require excellent fluid flow rates with very little flow-rate variations from one male-luer to another. In addition, Mackal's valve element design has a dead space hole on the rear end of the valve element. In blood collection applications, it is very difficult to satisfactorily flush the blood from the check valve, thereby causing concern for contamination. Furthermore, the Mackal check valve has no means to securely attach and lock intravenous administration lines or syringes to the valve, thereby requiring the clinician to tape the connectors together.

U.S. Pat. No. 4,683,916 to Raines discloses a normally closed automatic reflux valve for use in the administration of fluids and medicinal liquids in medical environments. The valve includes a two-part body having a male luer-lock on one part and female luer-lock on the other part. Both parts also have cylindrical container portions which, when connected, restrain a flexible valve disk. A pointed triangle in the cylindrical container portion of the male connector supports a central area of the disk which in turn is under pressure from a traverse bar mounted in the cylindrical portion of the female connector. The pressure between the triangle point and the bar is generally sufficient to restrain the disk against sideways movement. A small plastic plunger having an open cylindrical end and a pair of dependent legs is mounted on top of the disk and extends into the female luer-lock. When the tip of a syringe or male-luer connector engages the open cylindrical end of the plunger and presses it inward, he disk is flexed against the triangle to open the valve. When the injection device or male-luer connector is removed, the resiliency of the disk closes the valve. While Raines' valve has certain advantages, the thin flexible valve disk is prone to problems in certain conditions. In intravenous therapy applications using glucose or fat emulsions, the valve disk does not always seal properly when the male-luer connector is removed. The dripping of intravenous fluids out of the female luer of the valve during the term of the intravenous therapy is a concern among healthcare and infection control professionals as it leads to possible contamination.

U.S. Pat. No. 5,230,706 to Duquette discloses a valve assembly for use in needleless injection or infusion ports. Duquette's valve assembly includes a valve body containing a valve port, a valve plunger having a sealing ring or shoulder, and a spring. The spring urges the valve plunger towards the valve port so that the sealing ring or shoulder seals the valve port. The valve port is disclosed as a female luer-slip and the valve plunger has a stem which enters the luer slip when the valve is sealed. Insertion of a male luer-slip into the valve port engages the stem on the plunger and moves the plunger against the spring to open the valve. Upon removal of the male luer-slip, the spring urges the valve back into the sealing position. Duquette's valve assembly solves many of the problems addressed above. However, it requires a metal spring which undesirably will come in contact for extended periods of time with various intravenous fluids, antibiotics, and the like.

In U.S. Pat. No. 5,242,432 to DeFrank discloses a needleless valve adapter. The assembly includes a valve body having a stepped fluid passage and a valve member with a biasing means disposed within the fluid passage. The valve member has a stem and a shoulder which seals the fluid passage. The valve stem is pierceable so that the valve can be used with a needle, if desired. The valve stem may also be moved by the nozzle of a needleless syringe. The biasing means is disclosed in a first embodiment as being formed integral with the valve member. In an alternative embodiment, the biasing means is a separate metallic spring element. The DeFrank valve design encourages a needleless application, but, it allows the use of a hypodermic needle if desired. The optional use of a needle goes against the new regulations and protocol of compliance by OSHA. In addition, the valve element design would significantly reduce fluid-flow rates and make adequate blood flushing very difficult. Also, DeFrank's valve element design would make the priming of the valve to remove air-bubbles prior to intravenous therapy difficult.

My prior U.S. Pat. No. 5,395,348 discloses a needleless intravenous quick connect/disconnect assembly which includes a first cylindrical member having a female luer connector extending from one end and providing a fluid path to the interior of the first cylindrical member, wherein a first seat is formed in the first cylindrical member at the junction of the female luer and the cylindrical opening; a second cylindrical member having a male-luer connector extending from one end and providing a fluid path to the interior of the second cylindrical member, wherein a second seat is formed in the second cylindrical member at the junction of the male-luer and the cylindrical opening; and a valve member having an integral stem, sealing surface, and resilient one-piece body. The outer diameter of the first cylindrical member is slightly smaller than the inner diameter of the second cylindrical member so that it may fit snugly inside the second cylindrical member. At least two radially extending ramped protrusions extend from the outer surface of the first cylindrical member and a corresponding number of radial openings or recesses are provided in the second cylindrical member. In the assembled state, the stem of the resilient valve member extends into the female luer from the inside of the first cylindrical member, and the resilient body of the valve member engages the second seat in the second cylindrical member and biases the sealing surface against the first seat in the first cylindrical member, thereby blocking fluid communication between the female-luer and the interior of the first cylindrical member. The integral valve member is a stepped diameter cylinder having a hollow body and solid stem. The body has a larger diameter than the stem and the step between the body and the stem is frustroconical wherein the sealing surface is formed. The end of the stem is provided with a diametrical slot. An annular fluid passage exists between the valve member body and the cylindrical members. The second seat is preferably formed from a plurality of radically arranged vanes which enter the hollow body of the valve member and flare outward from it. Spaces between the vanes provide a fluid passage from the male-luer to the annular fluid passage surrounding the valve member body. When a male-luer is inserted into the female luer connector, the valve member stem is pressed partially into the first cylindrical member thereby moving the sealing surface away from the first seat and also moving either the diametrical slot in the valve member stem at least partially inside the first cylindrical member. Fluid is free to pass from the male luer through the diametrical slot in the valve member stem, out into the first cylindrical member, around the sealing ring, into the annular fluid passage surrounding the valve member body, through the spaces between the radial vanes, and through the male luer connector in the second cylindrical member. When a male luer is withdrawn from the female luer connector, the resilient body of the valve member biases the valve stem back into the female-luer connector and thereby moves the sealing surface against the first seat, closing the valve.

Despite the many improvements in the connector disclosed in my U.S. Pat. No. 5,395,348, the valve member inhibits optimal performance of a needleless valve during intravenous and blood collection applications in several ways. Due to the variations of male luer connectors around the world, the one-piece resilient valve stem member still restricts fluid-flow, and the variation of fluid flow from one connector to another was found to be unacceptable. Further, the hollow body of the one-piece valve member interferes with adequate blood flushing of the valve, as the hollow body has an open end or concavity in which fluid may accumulate without passing along the flow-stream through the connector.

SUMMARY OF THE INVENTION

It is therefore an object of the invention to provide a needleless medical injection port which is safe, efficacious, and easy to use.

It is also an object of the invention to provide an injection port valve system which is activated by any male luer connector without the use of adapters.

It is another object of the invention to provide an injection port which utilizes a luer lock connection and thereby eliminates the need to tape connectors together.

It is a further object of the invention to provide both luer activated and fluid pressure activated medical intravenous line connectors which achieve a high flow rate.

It is an additional object of the invention to provide luer activated medical intravenous line connectors which tolerate variations in male luer dimensions with little affect on the flow rate.

Another object of the invention is to provide both luer activated and fluid pressure activated medical intravenous line connectors which have good blood flushing characteristics.

A further object of the invention is to provide a medical IV line connector having a resilient valve member which is designed without "dead" spaces in which fluids may become entrapped.

An additional object of the invention is to provide luer activated medical intravenous line connectors with reduced priming volume relative to prior art luer activated medical intravenous line connectors.

A further object of the invention is to provide medical intravenous line connectors having components which are easily substituted during manufacture to provide either luer activated connectors or fluid pressure activated connectors.

Yet another object of the invention is to provide medical intravenous line connectors which are resistent to leaking even up to one hundred activations.

Still another object of the invention is to provide a medical IV line connector having a resilient valve member with means for repeatedly centering the valve relative to a sealing ring.

Even another object of the invention is to provide a medical IV line connector where debubbling is simply achieved.

In accordance with the objects stated above, a needleless IV line connector assembly is provided and a first embodiment thereof generally comprises: a first cylindrical member having a female luer connector (preferably a luer lock) extending from one end and providing a fluid path to the interior of the first cylindrical member, wherein a first sealing ring seat is formed in the first cylindrical member at the junction of the female luer and the cylindrical opening; a second cylindrical member having a male luer connector (preferably a luer lock) extending from one end and providing a fluid path to the interior of the second cylindrical member, wherein a second seat is formed in the second cylindrical member at the junction of the male luer and the cylindrical opening; and a two part valve member including a valve stem and a resilient valve body having an annular sealing surface. The outer diameter of the first cylindrical member is substantially the same as the inner diameter of the second cylindrical member so that it fits snugly inside the second cylindrical member. The outer surface of the first cylindrical member preferably includes at least two radially ramped protrusions while the second cylindrical member preferably includes a corresponding number of radial openings or recesses. One end of the valve stem has an axial bore and the other end of the valve stem has an axial stabilizing pin and a circumferential flange. The valve stem also has at least one radial bore which is in fluid communication with the axial bore. The valve body has an axial bore which receives the axial stabilizing pin and circumferential flange of the valve stem such that the two parts of the valve member snap together. When the valve member is assembled, the annular sealing surface of the valve body faces the valve stem.

A first embodiment of the connector is assembled by placing the stem of the valve member into the cylindrical opening of the first cylindrical member so that it enters the female luer connector and the annular sealing surface of the valve body rests against the first seat. The second cylindrical member is then placed over the first cylindrical member until the radially extending ramped protrusions lockingly engage the radial openings or recesses. In the assembled state, the stem of the valve member extends into the female luer from the inside of the first cylindrical member, and the resilient body of the valve member engages the second seat in the second cylindrical member and biases the annular sealing surface against the first seat in the first cylindrical member, thereby blocking fluid communication between the female luer and the interior of the first cylindrical member.

According to one embodiment of the valve member, the valve body is made of a flexible resilient material such as medical grade silicone or KRATON™, and has a substantially hour-glass bellowed profile. According to another embodiment of the valve member, the valve body is made of medical grade silicone having a Durometer of approximately 50 and is substantially frustroconical in profile. In both embodiments of the valve member, the valve stem is preferably made of rigid or semi-rigid thermoplastic (preferably clear ABS or polycarbonate) and is preferably provided with two diametrically opposed radial bores which are ramped toward and into the axial bore. The outer diameter of the valve body is smaller than the inner diameter of the first and second cylindrical members so that when the valve body is supported on the second seat, an annular fluid passage exists between the valve body and the cylindrical members. The second seat is preferably formed as a plurality of radially arranged vanes with steps which support the valve body. Spaces between the vanes provide a fluid passage from the male luer to the annular fluid passage surrounding the valve body.

According to another embodiment of the valve member, the relatively rigid valve stem is inserted in a mold and the relatively resilient valve body is molded around it. In still another embodiment of the valve member, the stem and valve body are injection molded as an integral unit. In this embodiment, preferably two different materials are injected into the mold. A first relatively rigid (when cured) material is injected to form the stem, and a second relatively resilient (when cured) material is injected into the same mold to form the body.

According to one embodiment of the cylindrical members, a plurality of circular ridges are provided between the vanes and the interior surface of the second cylindrical member, and the first cylindrical member is dimensioned to engage the ridges to provide a fluid-tight coupling of the first and second cylindrical members. According to another embodiment of the cylindrical members, an O-ring is provided in the space between the vanes and the interior surface of the second cylindrical member, and the first cylindrical member is dimensioned to engage the O-ring. In another embodiment of the cylindrical members, a single circular groove is provided between the vanes and the interior surface of the second cylindrical member, and the first cylindrical member is provided with an annular outer ring which sealingly engages the interior surface of the second cylindrical member. In still another embodiment of the cylindrical members, a single circular groove with inwardly tapered walls is provided between the vanes and the interior surface of the second cylindrical member, and the first cylindrical member is provided with a circular V-groove. When the pieces are assembled, the V-groove is pinched between the tapered walls. In still another embodiment of the cylindrical members, a single circular ridge with outwardly flared walls is provided between the vanes and the interior surface of the second cylindrical member, and the first cylindrical member is provided with a circular V-groove. When the pieces are assembled, the flared walls spread the V-groove.

A presently preferred embodiment of the connector assembly generally includes: a first coupling member having a female luer connector (preferably a luer lock) with a fluid path therethrough, a flange having a first sealing ring seat formed therein and a first mating means; a second coupling member having a male luer connector (preferably a luer lock) extending from one end and providing a fluid path to the fluid path of the female luer connector, the coupling member having a second mating means; and a valve member including a valve stem and a resilient valve body having an annular sealing surface. A valve body seat is formed in the interior of the second coupling member by a plurality of radially arranged vanes which extend substantially the entire length of the second coupling member above the male luer. The presently preferred embodiment of the connector assembly is assembled by placing the body of the valve member in the valve body seat of the second coupling member, placing the first coupling member over the valve stem so that the stem enters the female luer and the mating means of the flange on the first coupling member mates with the mating means of the second coupling member. While applying axial pressure to join the coupling members, sonic energy is applied to weld the mating means and hence the members together. Under the influence of sonic energy, the mating means melt at their point of contact and move towards each other to form a string fluid-tight fusion. As assembled in this fashion, the valve body is stabilized, centered, and biased towards the first sealing ring.

In the luer-activated embodiment of the invention, the length of the female luer of the assembly is chosen so that when a male luer is inserted into the female luer, the valve member stem is pushed towards the male luer of the assembly thereby moving the sealing surface of the valve body away from the first seat and also moving the radial openings in the valve stem at least partially inside the first cylindrical member. Fluid is thus free to pass through the axial opening of the valve stem and out through the radial openings of the valve stem into the annular fluid passage surrounding the valve body, through the spaces between the radial vanes, and through the male luer connector of the assembly. When opened, the valve member allows fluid flow in either direction, from the male luer to the female luer of the assembly or vice versa. When a male luer is withdrawn from the female luer connector, the resilient valve body biases the valve stem back into the female luer connector and also moves the sealing surface against the first seat, closing the valve.

In the fluid pressure activated embodiment of the invention, the length of the female luer of the assembly is chosen so that when a male luer is inserted into the female luer connector, the valve member stem is not engaged by the male luer. In this embodiment, fluid passing through the male luer with sufficient pressure causes the valve stem to move as described above.

11

According to one aspect of the invention, the second coupling member may be formed as a Y-site adapter rather than a male luer lock. According to another aspect of the invention, the second coupling member may be formed as a multiple access manifold coupled to a plurality of first coupling members and valve members.

Additional objects and advantages of the invention will become apparent to those skilled in the art upon reference to the detailed description in conjunction with the accompanying drawings.

BRIEF DESCRIPTION OF THE DRAWINGS

FIG. 7 is a view similar to FIG. 1 of a second embodiment of the invention;

FIG. 8 is a view similar to FIG. 4 of the second embodiment of the invention;

FIG. 13 is a view similar to FIG. 5 of a third embodiment of the invention;

FIG. 14 is a view similar to FIG. 13 of a fluid pressure activated version of the third embodiment of the invention;

FIG. 15 is a longitudinal cross-sectional view of a Y-adapter version of the third embodiment of the invention;

FIG. 16 is a longitudinal cross-sectional view of a multiple access intravenous manifold version of the third embodiment of the invention;

12

Figure 17:
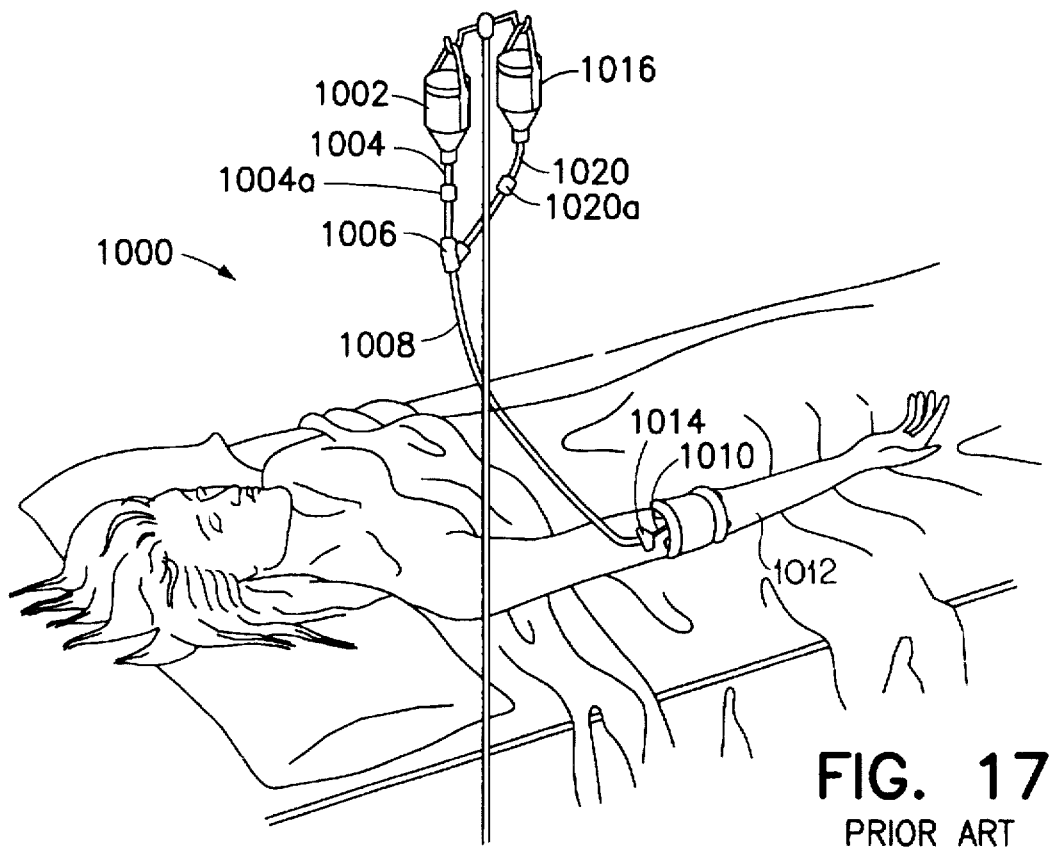
Figure 18:
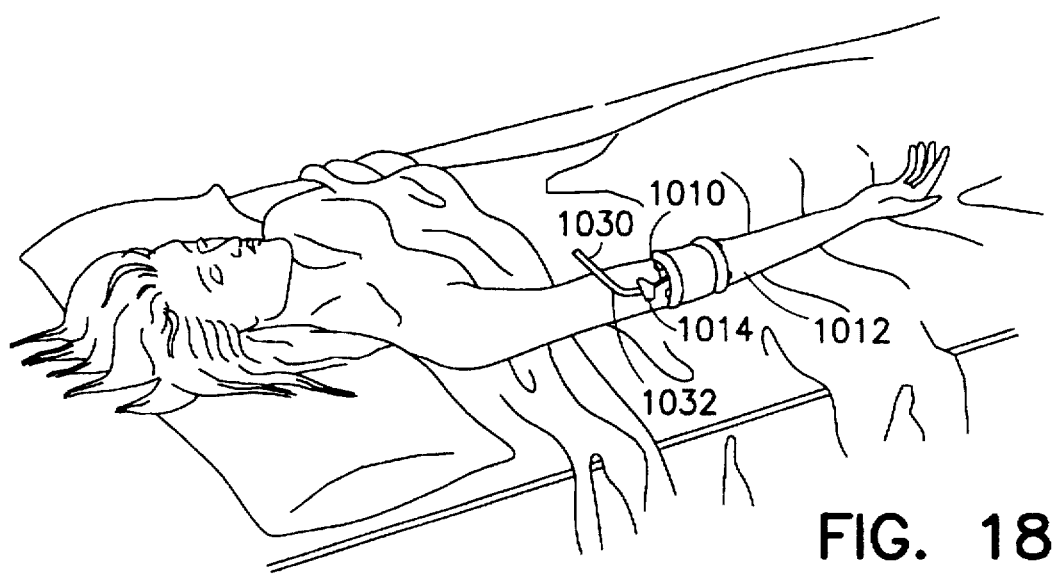
Figure 19:
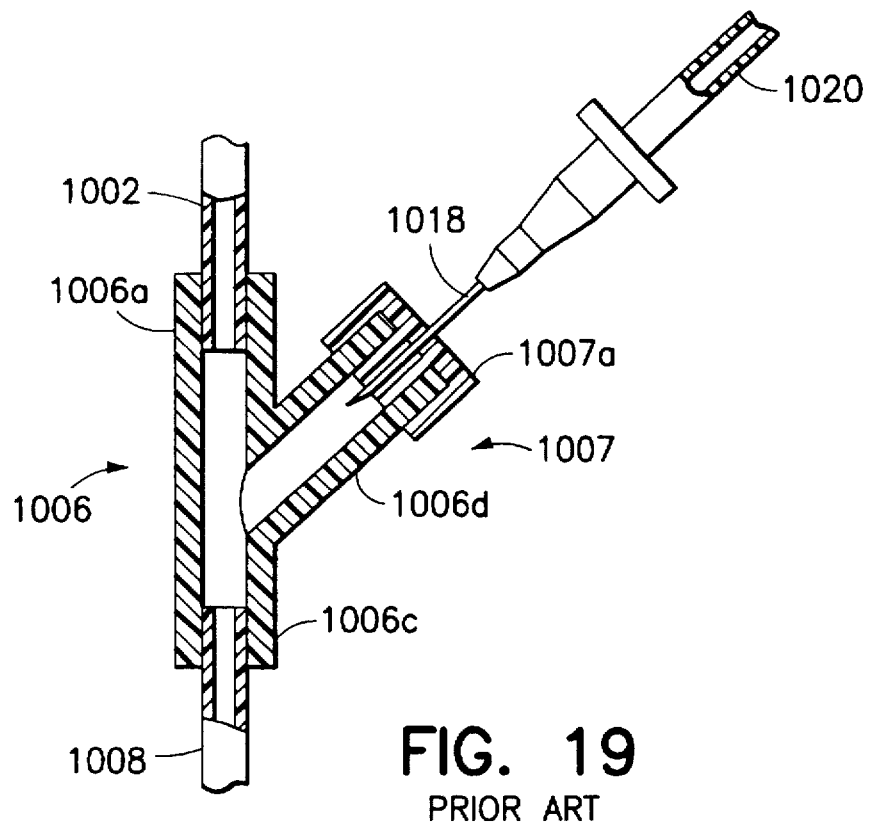
Figure 20:
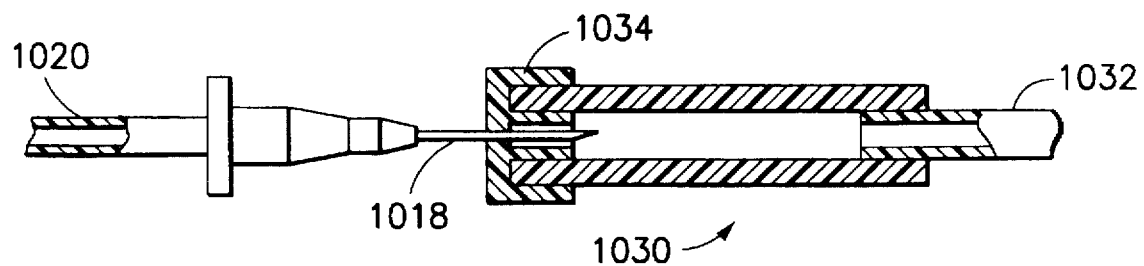

FIG. 17 is a schematic view of a prior art intravenous administration set coupled to a patient;

FIG. 18 is a view similar to FIG. 17 of a prior art "intermittent" intravenous administration set coupled to a patient;

FIG. 19 is a broken side elevation view, in partial section, of a prior art Y-injection site; and FIG. 20 is a broken side elevation view, in partial section, of a prior art heparin lock injection port.

DETAILED DESCRIPTION OF THE PREFERRED EMBODIMENTS

Figure 1:
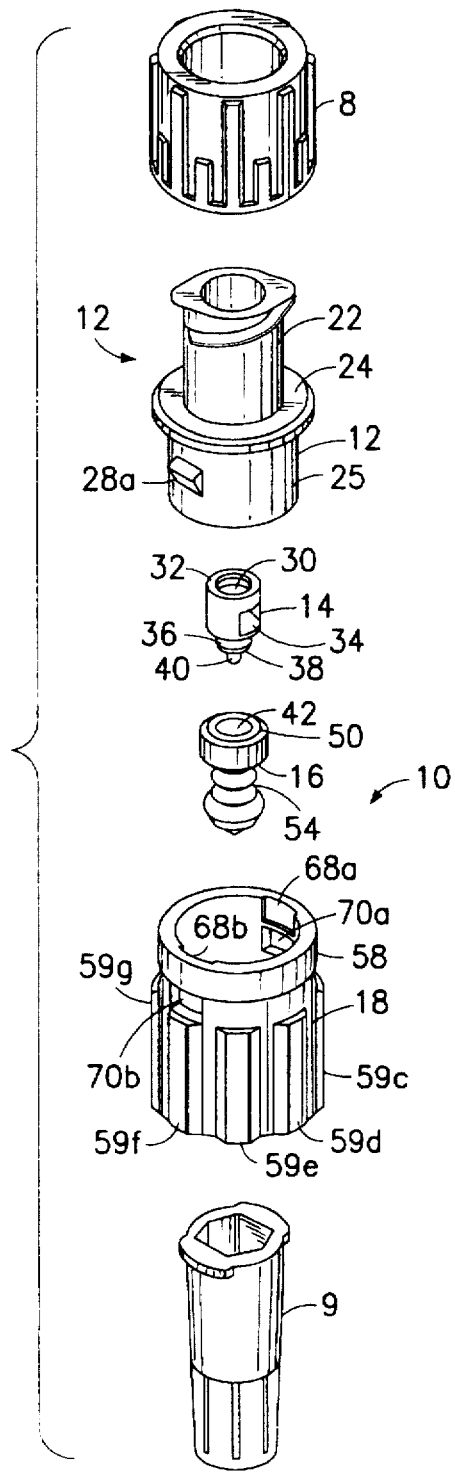
FIG. 1 is an exploded perspective view of a first embodiment of the invention including luer end caps.
Figure 2:
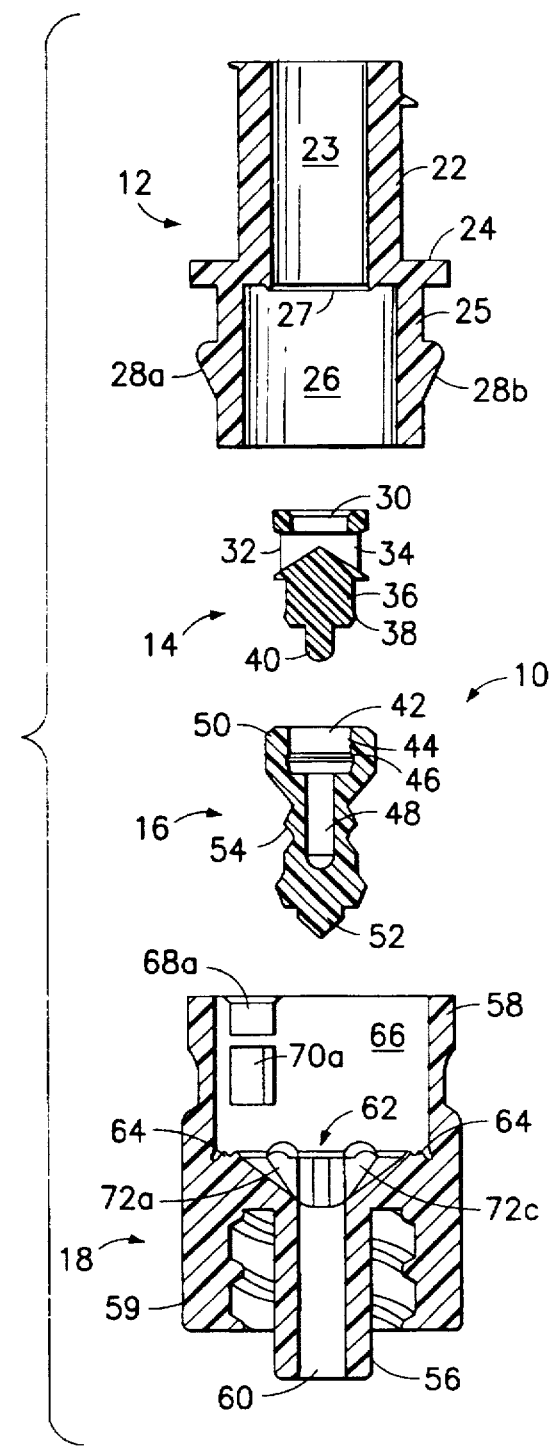
FIG. 2 is an exploded sectional view of the embodiment of FIG. 1 without end caps.
Figure 3:
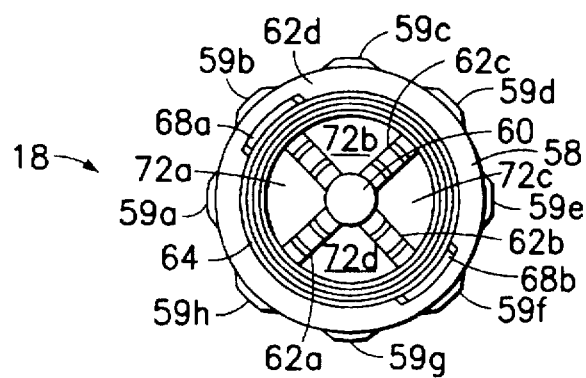
FIG. 3 is a top plan view of the second cylindrical member of FIGS. 1 and 2.

Referring now to FIGS. 1 through 3, a first embodiment of the quick-connect/disconnect device 10 for an IV administration line system includes four parts: a first cylindrical member 12, a valve stem 14, a resilient valve body 16, and a second cylindrical member 18.

The first cylindrical member 12 has a female luer connector 22 separated by a flange 24 from a cylinder 25 having a cylindrical interior space 26. Those skilled in the art will appreciate that the female luer 22 provides a fluid path 23 into the interior cylindrical space 26 of the cylinder 25. At the opening from the female luer into the cylindrical space 26, a seat which is preferably in the form of a slightly protruding annular ring 27 is formed and effectively surrounds the fluid path 23 entry from the female luer 22. The exterior surface of the cylinder 25 is preferably provided with locking means taking the form of two diametrically opposed radially extending ramped protrusions 28a, 28b. The first cylindrical portion is preferably made of molded co-polypropylene polymer such as EXXON Escorene #PD 9074 MED.

The valve stem 14 has an axial bore 30 at one end with a pair of ramped radial bores 32, 34 in fluid communication therewith, an intermediate reduced diameter portion 36 with a circumferential flange 38, and an axial stabilizing pin 40 at the other end. The valve stem 14 is preferably made of a rigid or semi-rigid plastic such as ABS or polycarbonate. According to a presently preferred embodiment, the axial bore 30 is circular and the radial bores 32, 34 are rectilinear. It is believed that this configuration enhances fluid flow through the bores as described in more detail below.

The valve body 16 has an axial bore 42 at one end. The axial bore 42 has a relatively large diameter portion 44 with an interior surface groove 46 and a relatively small diameter portion 48. An annular sealing surface 50 surrounds the axial bore 42. The other end of the valve body 16 has a conical tip 52. The overall profile of the valve body 16 is somewhat hour glass shaped with a relatively narrow waist 54 and is advantageously provided with a bellows-like surface to facilitated axial compression and expansion as described in more detail below. The valve body 16 is preferably made of a flexible resilient material such as medical grade silicone or KRATON™.

Figure 4:
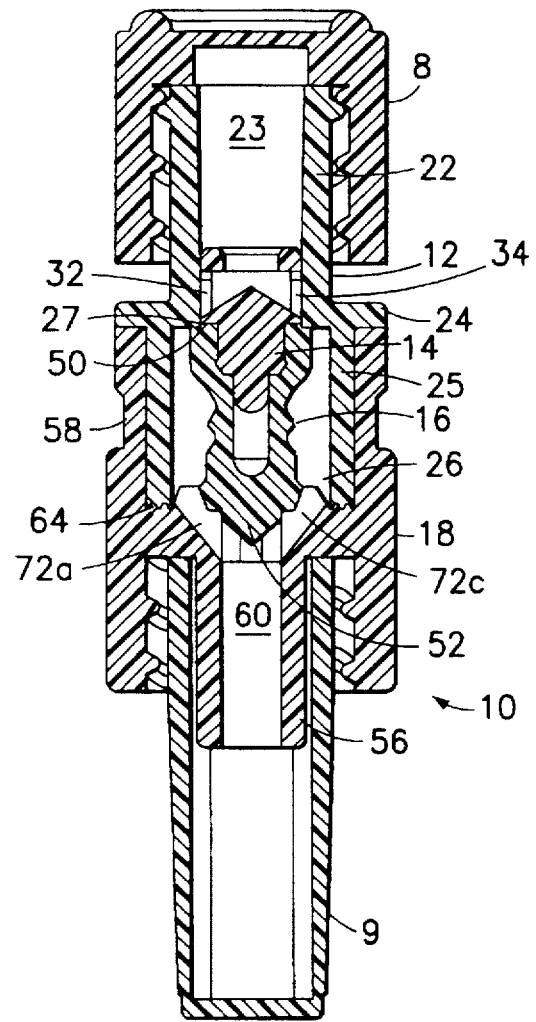
FIG. 4 is an assembled sectional view of the embodiment of FIGS. 1 and 2 including luer end caps.
Figure 5:
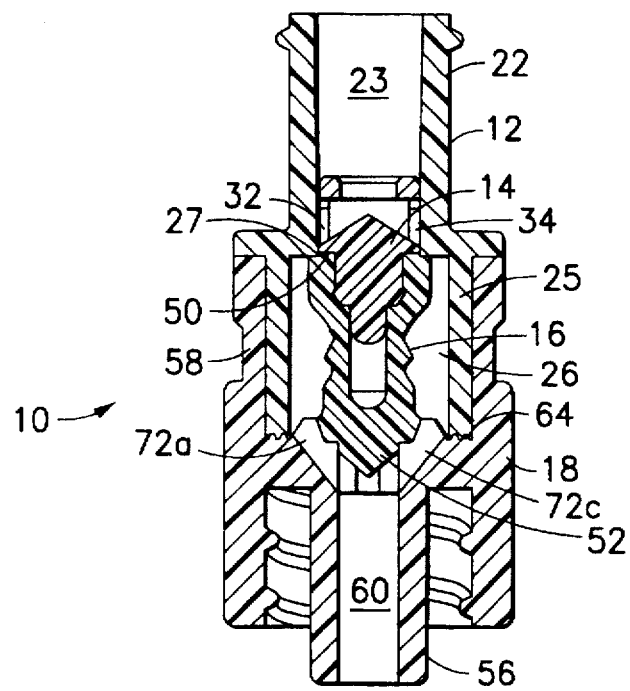
FIG. 5 is a view similar to FIG. 4 with the luer end caps removed.
Figure 6:
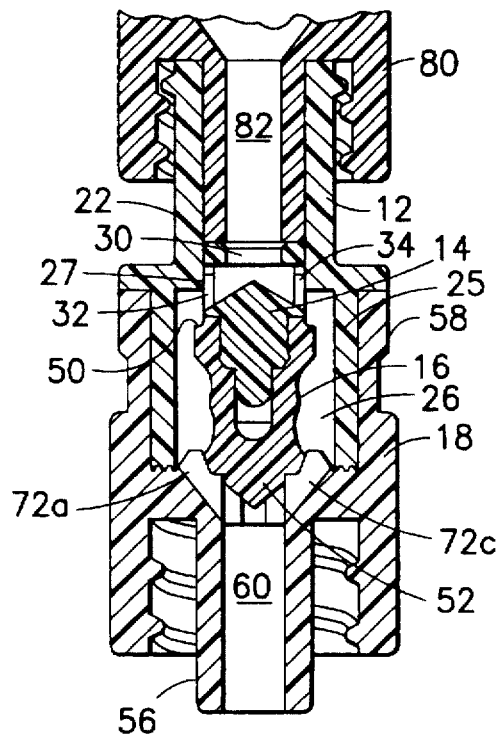
FIG. 6 is a view similar to FIG. 5 with an attached male luer forcing the valve member in the open position.
Figure 6A:
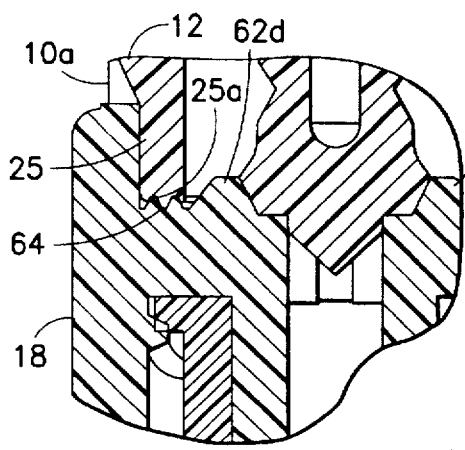
FIG. 6a is an enlarge broken sectional view of the fluid tight coupling of the cylindrical members of the embodiment of FIGS. 1–6.

The valve stem 14 and the valve body 16 snap together as shown in FIGS. 4–6. More specifically, the portion 44 of the bore 42 in the valve body 16 receives the intermediate portion 36 of the valve stem 14. The circumferential flange 38 has a diameter slightly larger than the diameter of the portion 44 of the bore 42. When the stem 14 is inserted into the body 16, the flange 38 stretches the resilient body 16 until the flange reaches the groove 46 in the bore 42. The groove 42 has a diameter just slightly smaller than the diameter of the flange 38. The pieces snap together when the flange 38 embraces the groove 46, forcing the groove 46 to expand. This inhibits the pieces from separating. The axial stabilizing pin 40 of the valve stem 14 is received by the small diameter portion 48 of the bore 42. It should be noted that length of the pin 40 is shorter than the length of the small diameter portion 48 of the bore 42.

The second cylindrical member 18 is preferably provided with a male luer connector 56 at one end and an open ended cylinder 58 at the other end. The male luer connector 56 has an interior fluid path 60 which terminates in a valve body seat 62 surrounded by circular ribs 64 inside the interior space 66 of the open ended cylinder 58. The interior space 66 is sized to receive the cylinder portion 25 of the first cylindrical member 12 and the circular ribs 64 are sized to fit snugly against the end of the cylinder 25 as shown in FIGS. 4-6. Two diametrically opposed longitudinal grooves 68a, 68b are provided on the interior surface of the open ended cylinder 58 for guiding the radially extending ramped protrusions 28a, 28b on the exterior surface of the cylinder portion 25 of the first cylindrical member 12 during assembly as described more fully below. The longitudinal grooves 68a, 68b terminate in second locking means which preferably take the form of radial openings 70a, 70b for receiving and locking the protrusions 28a, 28b as described in detail below. The exterior surface 59 of the male luer connector is provided with a plurality of longitudinally extending radially raised portions 59a–59h which act as a finger gripping surface when the assembly is twisted into connection with another fluid connector (not shown). The valve body seat 62 is composed of four equidistant radial vanes 62a–62d each of which step down in the radially inward direction. Spaces 72a–72d between the vanes 62a–62d provide a ramped fluid passage from the interior space 66 of the cylinder 58 to the fluid path 60 of the luer connector 56. The second cylindrical member is preferably made of clear molded polycarbonate, polystyrene, ABS, or styrene. Thus, the Durometer of the second cylindrical member is greater than the Durometer of the first cylindrical member. This aids in providing a fluid-tight seal between the members when they are assembled.

Assembly of the quick-connect/disconnect device 10 is described with reference to FIGS. 1–5. The valve stem 14 and the valve body 16 are mated as described above, and the valve stem 14 is inserted into the interior space 26 of the cylindrical portion 25 of the first cylindrical member 12 so that it enters the fluid path 23 of the female luer 22 and the sealing surface 50 of the valve body 16 rests against the annular ring 27. The cylinder portion 25 of the first cylindrical member 12 is then inserted into the open ended cylinder 58 of the second cylindrical member 18 so that the ramped protrusions 28a, 28b align with the longitudinal grooves 68a, 68b. The first cylindrical member 12 and the second cylindrical member 18 are pressed together until the ramped protrusions 28a, 28b snap into and lock with the radial openings 70a, 70b. In this regard, it will be appreciated that the cylindrical portion 25 and/or the open ended cylinder 58 are provided with sufficient resiliency so that the ramped protrusions 28a, 28b are biased radially inward as they are guided by the longitudinal grooves 68a, 68b and spring radially outward into the radial openings 70a, 70b. Further, it will be appreciated that the protrusions 28a, 28b are ramped in the direction to facilitate assembly and to impede or prevent disassembly. In the assembled state, as shown in FIGS. 4 and 5, the cylindrical portion 25 fully occupies the open ended cylinder 58 with the valve body 16 occupying the interior space 26 of the cylindrical portion 25. The end 52 of the valve body 16 is supported by the vanes 62a–62d with the steps in the vanes centering and stabilizing the valve body 16. The distance between the sealing surface 50 of the valve body 16 and the end 52 of the valve body is slightly larger than the distance between the vanes 62a–62d and the annular ring 27. Therefore, as assembled, the resilient valve body 16 biases the valve stem 14 into the fluid path 23 of the female luer 22 and the sealing surface 50 is biased against the annular ring 27 holding the valve in a closed position as shown in FIGS. 4 and 5. The end of the first cylindrical member 12 surrounds the vanes 62a–62d and abuts the circular ribs 64 in the second cylindrical member 18 providing a fluid tight coupling. As mentioned above, the difference in the Durometer of the two cylindrical members aids in providing the fluid tight seal. The assembled IV connector is preferably fitted with off-the-shelf luer end caps 8, 9 as shown in FIGS. 1 and 4 so that the fluid passages are kept clean and sterile during shipping and prior to use.

In normal operation, the male luer connector is connected to a female luer connector (not shown) of an IV administration device. As seen in FIG. 6, when a male luer 80 (shown in a broken segment) is coupled to the female luer connector 22, the valve stem 14 is pressed inward and thereby compresses the resilient valve body 16 against the vanes 62a–62d. In this position, the sealing surface 50 of the valve body 16 is moved away from the annular ring 27 in the cylindrical portion 25 of the first cylindrical member 12, and the radial bores 32, 34 are moved into communication with the interior space 26 of the cylindrical portion 25. A fluid path is thereby established from the interior 82 of luer 80 through the axial bore 30, the radial bores 32, 34, through the interior space 26, around the valve body 16, through the spaces 72a–72d between vanes 62a–62d and into the fluid path 60 of luer 56. It will be appreciated that the fluid path is bidirectional and that fluid can flow from luer 56 to luer 80 as easily as from luer 80 to luer 56. The relatively large dimensions of the axial bore 30 and radial bores 32, 34 permit a very high fluid flow rate and a relatively consistent fluid flow rate regardless of minor variations in the size of the luer 80. The resilient valve body 16 returns the valve to the closed position shown in FIGS. 4 and 5 when the luer 80 is uncoupled from the luer 22.

Figure 6B:
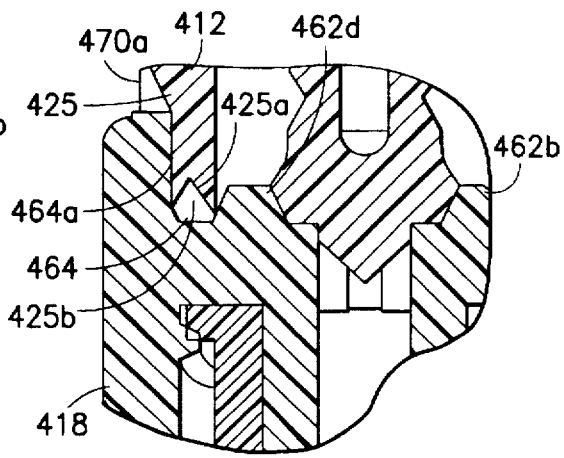
FIG. 6b is a first alternate embodiment of the fluid tight coupling.

Referring now to FIGS. 6a–6d, several embodiment of a fluid tight connection of the first and second cylindrical members are shown. As mentioned above and as shown in greater detail in FIG. 6a, according to one embodiment, the end 25a of the first cylindrical member 12 abuts the circular ribs 64 in the second cylindrical member 18 providing a fluid tight coupling. In another embodiment of the cylindrical members 412, 418, as shown in FIG. 6b, a single circular groove or seat 464 with inwardly tapered walls 464a is provided between the vanes 462a–d and the interior surface of the second cylindrical member 418, and the end 425a of the first cylindrical member 412 is provided with a circular V-groove 425b. When the pieces are assembled, the V-groove 425b is pinched between the tapered walls 464a.

Figure 6C:
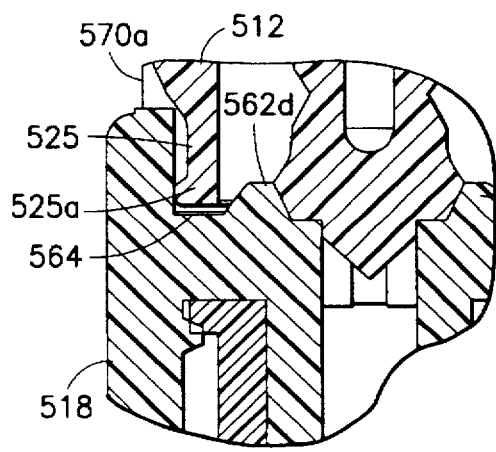
FIG. 6c is a second alternate embodiment of the fluid tight coupling.
Figure 6D:
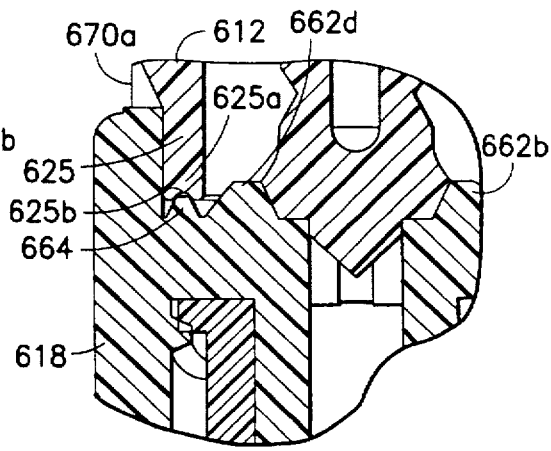
FIG. 6d is a third alternate embodiment of the fluid tight coupling.

In a third embodiment of the fluid tight connection, as shown in FIG. 6c, a single circular groove 564 is provided between the vanes 562a–d and the interior surface of the second cylindrical member 518, and the end 525a of the first cylindrical member 512 is provided with an annular outer ring which sealingly engages the interior surface of the second cylindrical member 518. In still another embodiment of the cylindrical members, shown in FIG. 6d, a single circular ridge 664 with outwardly flared walls is provided between the vanes 662a–d and the interior surface of the second cylindrical member 618, and the end 625a of the first cylindrical member 612 is provided with a circular V-groove 625b. When the pieces are assembled, the flared walls spread the V-groove 625b.

Figure 9:
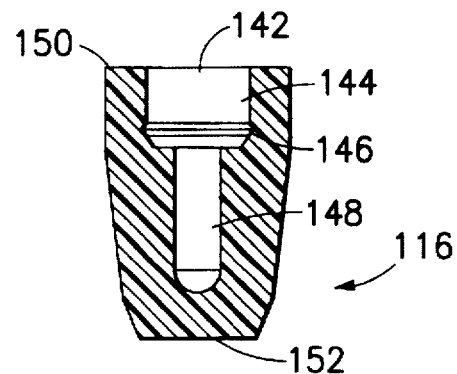
FIG. 9 is a sectional view of the valve body of the second embodiment of the invention.

Turning now to FIGS. 7-9, a second embodiment of an administration line connector 110 is shown. The connector 110 has five components: a first cylindrical member 12, a valve stem 14, a valve body 116, an O-ring 117, and a second cylindrical member 118 (identical components being referenced with the identical numerals as in FIGS. 1-6 above). The valve body 116 differs from the valve body 16 described above in that its overall shape is frustroconical with a broad end serving as a sealing surface 150 and a narrow end 152 serving as a tip. The axial bore 142 in the valve body 116 is substantially identical to the axial bore 42 described above and similar reference numerals refer to similar features which enable the valve body and the valve stem to snap together as described above. The valve body 116 is preferably made of silicone having a Durometer of about 50.

The second cylindrical member 118 is substantially the same as the second cylindrical member 18 described above except for the configuration of the vanes 162a-162d and the lack of circular ridges surrounding the vanes. In order to accommodate the valve body 116 and the O-ring 117 as shown in FIG. 8, the vanes 162a-162d have a taller step than the vanes 62a-62d described above.

The connector 110 is assembled in substantially the same manner as the connector 10 described above, except that the O-ring 117, preferably formed from silicone, is placed in the annular space surrounding the vanes 162a-162d prior to inserting the first cylindrical member 12 into the second cylindrical member 118. As can be appreciated from FIG. 8, the taller step in the vanes 162a-162d help to stabilize and center the tip 152 of the valve body 116 as well as to locate the O-ring 117. The O-ring 117 provides a fluid-tight coupling of the first cylindrical member 12 and the second cylindrical member 118. Operation of the connector 110 is substantially the same as the operation of the connector 10 described above.

Figure 9A:
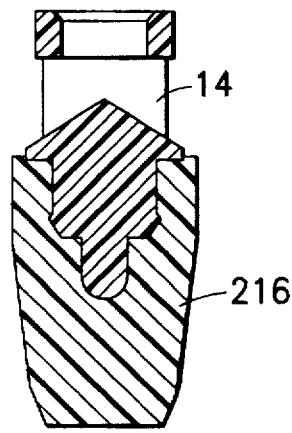
FIG. 9a is a view similar to FIG. 9 of a first alternate embodiment of the valve body and valve stem of the second embodiment of the invention.
Figure 9B:
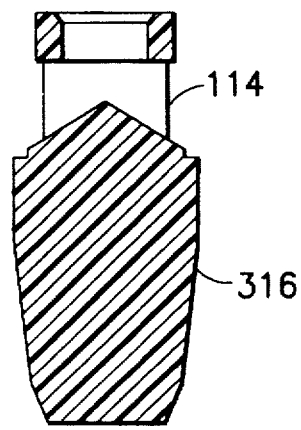
FIG. 9b is a view similar to FIG. 9a of a second alternate embodiment of the valve body and valve stem of the second embodiment of the invention.

The valve body 116 shown in FIGS. 8 and 9 is easier to manufacture than the valve body 16 shown in FIGS. 1-6 and it is believed to offer better performance. As shown in, FIGS. 8 and 9, and as described above, the valve body 116 and valve stem 14 are separate pieces that snap together. Referring now to FIGS. 9a and 9b the valve assembly according to the invention may be advantageously manufactured as an integral member. According to one alternate embodiment of the valve member, as shown in FIG. 9a, the relatively rigid valve stem 14 is inserted into a mold and the relatively resilient valve body 216 is molded around it. This forms a relatively integral valve member. In still another embodiment of the valve member, as shown in FIG. 9b, the stem 114 and the valve body 316 are injection molded as an integral unit. In this embodiment, preferably two different materials are injected into the mold. A first relatively rigid (when cured) material is injected to form the stem 114, and a second relatively resilient (when cured) material is injected into the same mold to form the body 316.

Figure 10:
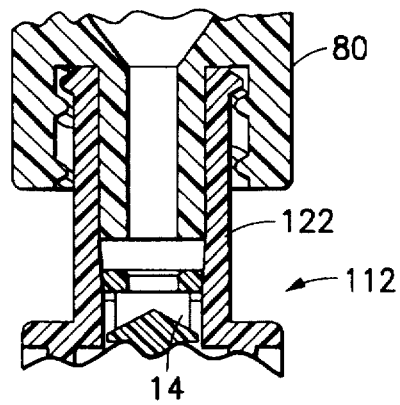
FIG. 10 is a broken sectional view of fluid pressure activated valve according to the invention with a male luer inserted.

As described above, the valves in both connectors 10 and 110 are activated by the end of a male luer engaging the valve stem 14. However, both connectors 10 and 110 can be easily modified so that the valve is opened by fluid pressure rather than the presence of a male luer. As shown in FIG. 10, a first cylindrical member 112 having a longer female luer 122 prevents the end of a male luer 80 from engaging the valve stem 14. In the embodiment shown in FIG. 10, the valve remains in the closed position until fluid flows through the luer 80 with sufficient pressure to move the stem 14. It is believed that the configuration of the axial bore 30 and the radial bores 32, 34, as well as the ramped nature of the radial bores renders the stem 14 more amenable to movement by the pressure of fluid. It will be noted that the arrangement shown in FIG. 10 is essentially a one-way valve since the valve will only open when fluid flows in one direction, i.e. out of the luer 80. Those skilled in the art will appreciate that in some applications it is advantageous to provide such a one way valve and that in some applications it is advantageous that the valve remain closed until fluid is flowing.

Figure 11:
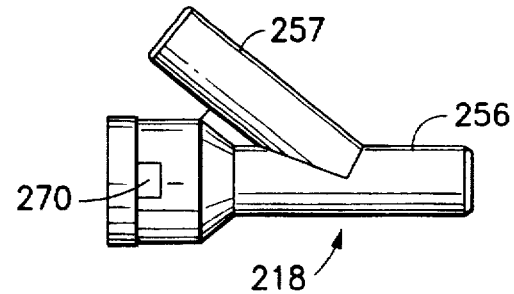
FIG. 11 is a side elevation view of a second cylindrical member formed as a Y-site according to the invention.

Turning now to FIG. 11, those skilled in the art will appreciate that any of the above described embodiments may be provided with a Y-site adapter 218. The Y-site adapter 218 shown in FIG. 11 replaces the second cylindrical member 18, 118 in the assemblies shown in FIGS. 1 and 7. Consequently, it has an interior portion substantially the same as the interior of cylindrical member 18 or 118 and includes a pair of radial openings 270a for mating with a first cylindrical member 12 or 112 as described above. The Y-site adapter has two fluid connectors 256 and 257 which define fluid paths without valves; although valves could be provided on these connectors as well.

Figure 12:
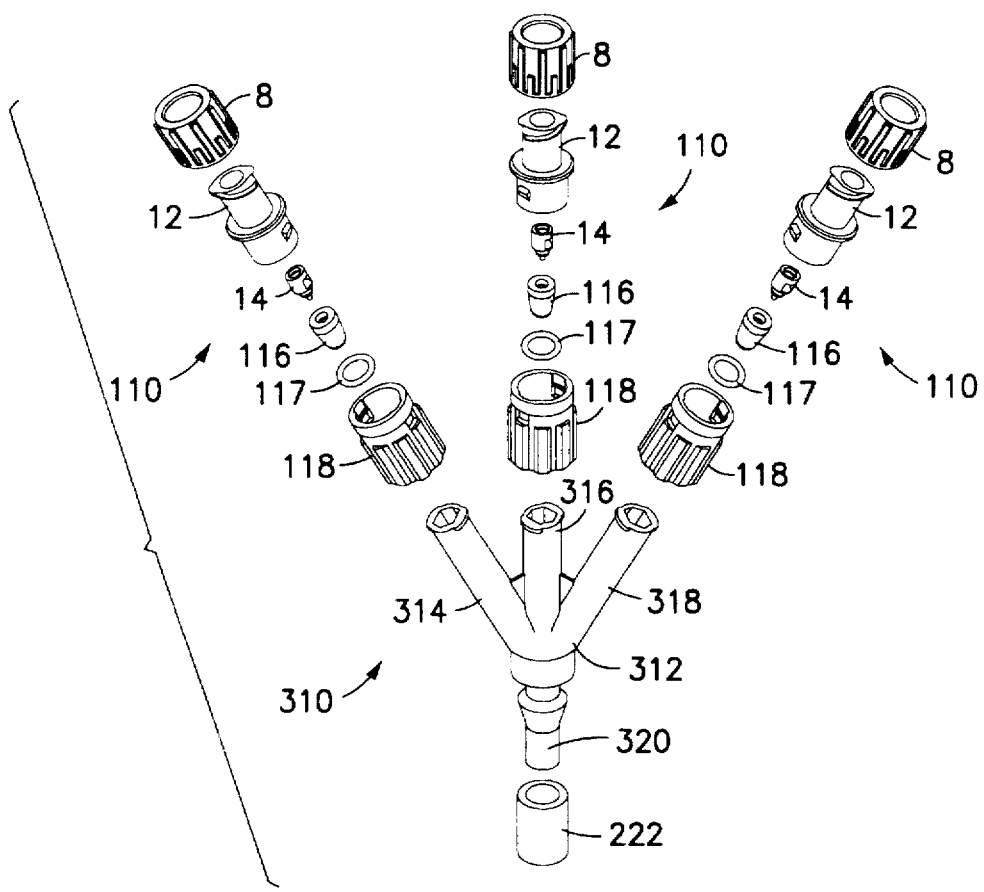
FIG. 12 is an exploded perspective view of a multiple access IV manifold according to the invention.

FIG. 12 illustrates a multiple access IV manifold 310 according to the invention. The multiple access manifold is useful for multiple infusion of drugs, medications and other liquids and particularly for the administration of anesthesia. The manifold 310 has a body 312 with three female luer inlets 314, 316, 318 and a male luer outlet 320. A connector 110 as described above is coupled to each of the female luer inlets 314, 316, 318 and a snap-on threaded member 322 is attached to the male luer outlet 320.

Figure 13A:
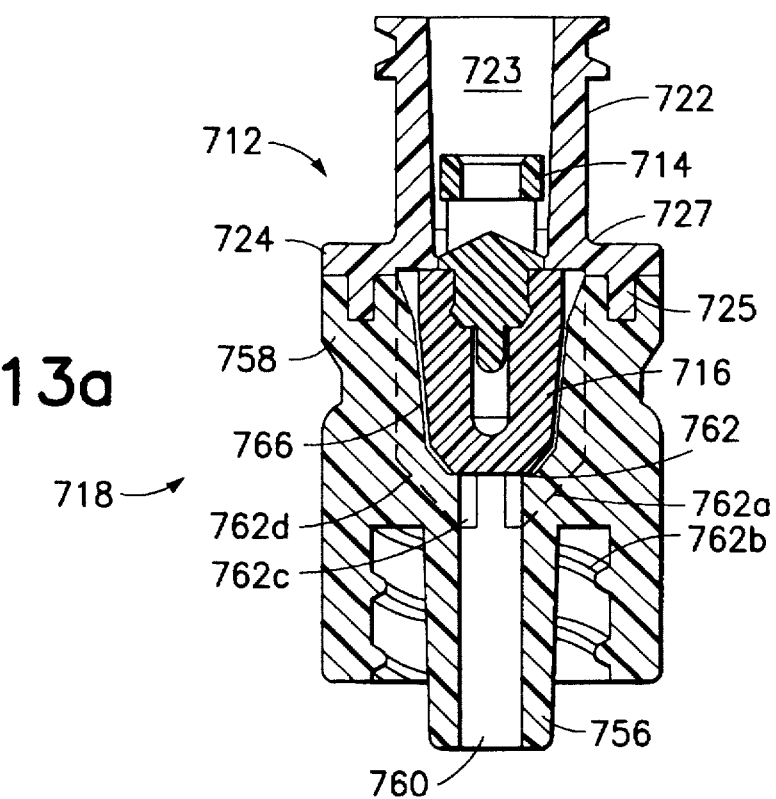
FIGS. 13a and 13b are views similar to FIG. 13 of the third embodiment of the invention after sonic welding and during activation respectively.
Figure 13B:
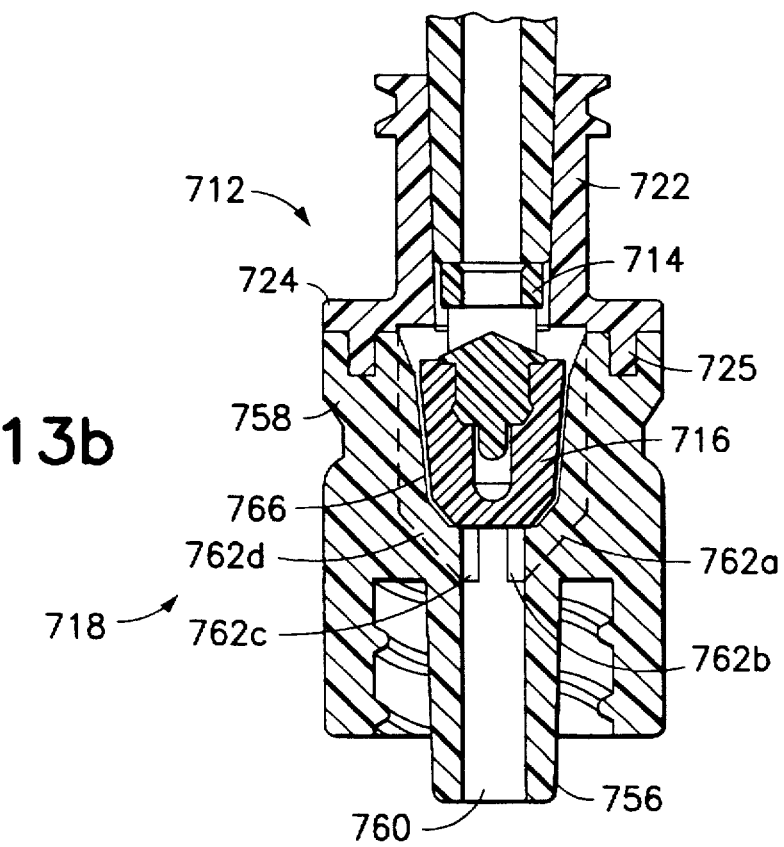

Turning now to FIG. 13, a presently preferred embodiment of the connector assembly 700 generally includes: a first coupling member 712, a valve stem 714, a resilient valve body 716, and a second coupling member 718. The first coupling member 712 is a female luer connector (preferably a luer lock) 722 having a flange 724 from which extends a cylindrical mating means 725 with a tapered edge 725a. The female luer connector 722 provides a fluid path 723 to the interior 726 of the cylindrical mating means 725. At the opening from the female luer into the cylindrical space 726, a first sealing ring seat 727 is formed. The valve stem 714 and the resilient body 716 are substantially the same as those described with reference to FIG. 9 and the valve members of FIGS. 9a and 9b may also be used in this embodiment. The second coupling member 718 has a male luer connector (preferably a luer lock) 756 at one end and an open ended cylinder 758 at the other end. The male luer 756 has an interior fluid path 760 which terminates in a valve body seat 762 inside the interior space 766 of the open ended cylinder 758. The valve body seat 762 includes a plurality of substantially L-shaped vanes 762a-762d which extend substantially along the entire length of the interior 766 of the cylinder 758 above the male luer 756. These vanes serve the function of consistently centering the valve in the seat after activation (see FIGS. 13a and 13b), such that no leakage is experienced even after numerous (e.g., one hundred) activations. An annular channel mating means 770 is provided at the end of the cylinder 758 and is dimensioned to receive the cylindrical mating means 725 of the first coupling member 712.

The connector assembly 700 of FIG. 13 is assembled by placing the body 716 of the valve member in the valve body seat 762 of the second coupling member 718, placing the first coupling member 712 over the valve stem 714 so that the stem enters the female luer 722 and the tapered edge 725a of the cylindrical mating means 725 rests inside the annular channel 770 of the second coupling member 718. While applying axial pressure to the first and second coupling members, the mating means and the first and second coupling members are welded by the application of sonic energy applied to weld the members together. Indeed, under the influence of sonic energy, the cylindrical members melt at their point of contact and move towards each other to form a string fluid-tight fusion. As assembled in this fashion, and as seen in FIG. 13a, the valve body 716 is stabilized, centered, and biased towards the first sealing ring 727.

In use, as seen in FIG. 13b, when a male luer is inserted into the female luer 722 of the first coupling member 712, the rigid or semi-rigid valve stem 714 is pushed downward, causing the top of the resilient valve body 716 to unseat from the sealing ring 727 of the first coupling member 712. In addition, as the resilient valve body 716 is compressed axially, the valve body tends to expand radially, just slightly, into the flow path spaces between the vanes 762. This expansion is illustrated in a slightly exaggerated form by the dotted lines in FIG. 13b for purposes of explanation only, and it will be appreciated that the valve body does not inhibit flow through the line connector device.

FIG. 14 shows a slightly different embodiment of a connector 700'. In this embodiment, the female luer 722' is longer than the luer 722 shown in FIG. 13 so that the valve is pressure activated as described above with reference to FIG. 10. In addition, the mating relationship of the first coupling member 712' and the second coupling member 718' is reversed. That is, the first coupling member 712' is provided with an annular channel 770' in the flange 724' and the second coupling member 718' is provided with a mating cylinder 725' having a tapered edge 725a'. Those skilled in the art will appreciate that the connector 700' is otherwise substantially the same as the connector 700 and that it is assembled in substantially the same way.

FIG. 15 shows a Y-site connector 800 based on the connector 700 described above. The Y-site connector 800 has a Y-site adapter 818 which replaces the second coupling member 718 shown in FIG. 13. The end of the Y-site adapter 818 which couples with the first coupling member 712 is substantially the same as the second coupling member 718 described above. It includes an open ended cylinder 858 and a valve body seat 862 inside the interior space 866 of the open ended cylinder 858. The other end of the Y-site adaptor 818 is provided with two fluid connectors 856, 857 which provide fluid paths in communication with each other as well as with the interior 866 of the cylinder 858. The valve body seat 862 includes a plurality of substantially L-shaped vanes 862a–862d which extend substantially along the entire length of the interior 866 of the cylinder 858 above the fluid connector 856. An annular channel 870 is provided at the end of the cylinder 858 and is dimensioned to receive the cylinder 725 of the first cylindrical member 712.

Turning now to FIG. 16, an IV manifold 900 utilizing connectors or the type described above with reference to FIGS. 13 and 14 is shown. The IV manifold 900 includes a body 910 having a male luer connector 956 at one end thereof and a plurality of second coupling members 918a–918d at different locations on the body 910. As shown in FIG. 16, the body 910 is a substantially tube-like member with one of the second coupling members 918a at an end opposite to the male luer 956 with the body 910, the male luer 956, and the second coupling member 918a being substantially coaxially aligned. Three other second coupling members 918b, 918c, and 918d are arranged substantially perpendicular to the body 910 and spaced along the length of the body 910. Each of the second coupling members 918a–918d is provided with a valve assembly and a corresponding first coupling member 912a–912d which are assembled in substantially the same manner as the connector 700 described above. The manifold 900 therefore provides four valved female luer connectors feeding into one male luer connector 956.

It should be appreciated by those skilled in the art that all embodiments of the IV administration line connectors described utilize valves with a rigid or semi-rigid top portion, and a flexible, resilient bottom portion. The valves as constructed, when compressed axially, expand radially at their flexible, resilient bottom portion. However, with the provided construction, the expansion of the flexible, resilient bottom portion is directed into one or both of a sealed opening between the rigid and flexible portions of the valve (except with the embodiments of FIGS. 9a and 9b where the opening is not present), and/or into the flow path. To the extent that the expansion is into the flow path (which in the case of FIGS. 13–15 is between the vanes), the flow path at that location is sufficiently large such that no effect on fluid flow occurs. By constructing the valve in this manner, as opposed to the manner of the prior art, no "dead" spaces are provided which could entrap blood; i.e., there are no concavities connected to, but between or off of the fluid flow paths where blood could gather, and where it would be difficult to flush the blood out. In addition, with no "dead" spaces, debubbling is easily accomplished and the priming volume is kept to a minimum.

There have been described and illustrated herein several embodiments of medical IV administration line connectors. While particular embodiments of the invention have been described, it is not intended that the invention be limited thereby, as it is intended that the invention be as broad in scope as the art will allow. Thus, it will be appreciated by those skilled in the art that the term "IV fluid" is intended to be understood in a broad sense to include blood or blood products, and the term "administration" is used in its broad sense to include the dispensing or collection of the "IV fluid". Further, while the connectors are illustrated as preferably having a female luer lock on one end, and a male luer lock on the other end, it will be appreciated that, although not preferred, simple luer slips could be utilized in lieu of luer locks. It will also be understood that while one end of the connector must be a female coupling, it is not necessary that the other end of the connector be a male coupling. Moreover, while certain embodiments connector assembly have been shown as having two cylindrical portions, one of which fits inside the other, it will be appreciated that either cylindrical portion could extend around the other provided that a cylindrical space is established for the biased valve member. In addition, while the locking and coupling of one embodiment of the first cylindrical and second cylindrical members is disclosed as a press- and snap-fit with ramped radial protrusions entering radial bores, it will be understood that other types of coupling such as screw coupling, solvent bonding, etc. could be used as well. Moreover, while the valve member seat has been disclosed as having four radial vanes, it will be understood with the benefit of the instant disclosure that the essence of the valve member seat is to provide a stable support for the valve member body while also providing a fluid path into the male luer. Other types of valve member seats having these features could be substituted without departing from the spirit of the invention. Therefore, it will be appreciated by those skilled in the art that yet other modifications could be made to the provided invention without deviating from its spirit and scope as so claimed.

I claim:

1. A fluid line connection assembly for coupling to and uncoupling from a first fluid pathway which terminates in a first male luer, the fluid line connection assembly comprising:

a) a first coupling member having a first female luer at a first end of said first coupling member, and a first mating structure;

b) a valve member having a stem and a resilient body with a sealing surface, said valve member disposed relative to said first coupling member with said stem extending into said first female luer, said stem having at least one axial bore and at least one radial bore, said at least one axial bore being in fluid communication with said at least one radial bore, said axial bore having an axis and said radial bore having a surface which forms and angle with said axis, said angle being greater than ninety degrees; and c) a second coupling member having an open generally cylindrical chamber with a valve member support, a first fluid coupling member in fluid communication with said cylindrical chamber, and a second mating structure for mating and coupling with said first mating structure, said second coupling member being coupled to said first coupling member with said valve member support supporting said resilient body of said valve member such that said sealing surface is biased against said first female luer thereby blocking fluid communication between said female luer and said first cylindrical chamber.

2. A fluid line connection assembly according to claim 1, wherein:

said first female luer and said stem extending into said first female luer are sized such that, upon coupling the first male luer to said first female luer, the first male luer engages said stem and moves said stem toward said second coupling member, thereby compressing said resilient body, moving said sealing surface away from said female luer, and opening fluid communication between said female luer and said cylindrical chamber, and upon uncoupling the first male luer from said first female luer, the first male luer disengages said stem and said resilient body expands towards said female luer such that said sealing surface contacts said female luer and blocks fluid communication between said female luer and said cylindrical chamber.

3. A fluid line connection assembly according to claim 1, wherein:

said first female luer and said stem extending into said first female luer are sized such that upon coupling the first male luer to said first female luer, the first male luer does not move said stem, but upon introducing fluid under pressure into said first male luer, fluid engages said stem and moves said stem toward said second coupling member, thereby compressing said resilient body, moving said sealing surface away from said female luer, and opening fluid communication between said female luer and said cylindrical chamber, and upon ceasing application of pressure to the fluid, the fluid disengages said stem and said resilient body expands towards said female luer such that said sealing surface contacts said female luer and blocks fluid communication between said female luer and said cylindrical chamber.

4. A fluid line connection assembly according to claim 1, wherein:

said valve member stem has a plurality of radial bores in fluid communication with said axial bore, and when said sealing surface is moved away from said first female luer, fluid communication between said first female luer and said cylindrical chamber is through said axial bore and said plurality of radial bores.

5. A fluid line connection assembly according to claim 1, wherein:

said stem and said resilient body are separate mating pieces, and said stem is relatively rigid compared to said resilient body.

6. A fluid line connection assembly according to claim 5, wherein:

said stem is formed from a rigid or semi-rigid material.

7. A fluid line connection assembly according to claim 1, wherein:

said resilient body is formed from a silicone.

8. A fluid line connection assembly according to claim 1, wherein:

said resilient body has a bellows profile.

9. A fluid line connection assembly according to claim 1, wherein:

said valve member support includes a fluid passage in fluid communication with said first fluid coupling member.

10. A fluid line connection assembly according to claim 9, wherein:

said valve member support comprises a plurality of radial vanes and said fluid passage comprises a space between said radial vanes.

11. A fluid line connection assembly according to claim 10, wherein:

said radial vanes have steps and said resilient body is supported by said steps.

12. A fluid line connection assembly according to claim 5, wherein:

said body has an axial bore into which said stem fits.

13. A fluid line connection assembly according to claim 4, wherein:

said plurality of radial bores are ramped away from said axial bore.

14. A fluid line connection assembly according to claim 1, wherein:

said first mating structure includes a cylinder dimensioned to fit inside said cylindrical chamber; and said second mating structure includes annular engagement means for sealingly engaging a distal end of said cylinder.

15. A fluid line connection assembly according to claim 14, further comprising:

d) an O-ring between said first and second mating structures.

16. A fluid line connection assembly according to claim 14, wherein:

said annular engagement means includes a plurality of circular ridges which sealingly engage said distal end of said cylinder.

17. A fluid line connection assembly according to claim 14, wherein:

said annular engagement means includes a tapered circular groove.

18. A fluid line connection assembly according to claim 17, wherein:

said distal end of said cylinder has a V-shaped groove.

19. A fluid line connection assembly according to claim 14, wherein:

said distal end of said cylinder has an annular ridge.

20. A fluid line connection assembly according to claim 14, wherein:

said annular engagement means includes a circular ridge.

21. A fluid line connection assembly according to claim 20, wherein:

said distal end of said cylinder has a V-shaped groove which is engaged by said circular ridge.

22. A fluid line connection assembly according to claim 14, wherein:

one of said cylinder and said cylindrical chamber is provided with a ramped projection and the other of said cylinder and said cylindrical chamber is provided with a recess or hole for receiving said ramped projection.

23. A fluid line connection assembly according to claim 1, wherein:

one of said first mating structure and said second mating structure includes an annular channel; and the other of said first mating structure and said second mating structure includes a cylinder dimensioned to fit inside said annular channel.

24. A fluid line connection assembly according to claim 23, wherein:

said first mating structure and said second mating structure are sonically welded.

25. A fluid line connection assembly according to claim 1, wherein:

said valve stem is insert molded into said valve body.

26. A fluid line connection assembly according to claim 1, wherein:

said valve stem and said valve body are molded as an integral piece.

27. A fluid line connection assembly according to claim 5, wherein:

said sealing surface of said valve member is a frustroconical portion of said resilient body.

28. A fluid line connection assembly according to claim 1, wherein:

said valve member support includes a plurality of vanes extending substantially the entire length of said cylindrical chamber.

29. A fluid line connection assembly according to claim 1, wherein:

said first fluid coupling member includes one of a Y-site adapter, an IV manifold and a male luer.

30. A fluid line connection assembly for coupling to and uncoupling from a first fluid pathway which terminates in a first male luer, the fluid line connection assembly comprising:

a) a first coupling member having a first female luer at a first end of said first coupling member, and a first mating structure;

b) a valve member having a substantially rigid stem with a bore and a substantially resilient body with a sealing surface, said valve member disposed relative to said first coupling member with said stem extending into said first female luer; and c) a second coupling member having an open generally cylindrical chamber with a valve member support, a first fluid coupling member in fluid communication with said cylindrical chamber, and a second mating structure for mating and coupling with said first mating structure, said second coupling member being coupled to said first coupling member with said valve member support supporting said resilient body of said valve member such that said sealing surface is biased against said first female luer thereby blocking fluid communication between said female luer and said first cylindrical chamber, wherein when said rigid stem is pushed toward said second coupling member, said substantially resilient body is axially compressed, and said substantially resilient body having a substantially solid portion presenting to said valve member support such that a fluid flow path through said fluid line connection assembly is established substantially without dead space.

31. A fluid line connection assembly according to claim 30, wherein:

said valve member is constructed with substantially no concavities in which where blood could gather, and where it would be difficult to flush the blood out.

32. A fluid line connection assembly according to claim 30, wherein:

said stem and said resilient body are separate mating pieces, and said substantially resilient body has an axial bore into which said stem extends.

33. A fluid line connection assembly according to claim 30, wherein:

said valve stem is insert molded into said resilient body.

34. A fluid line connection assembly according to claim 30, wherein:

said valve stem and said resilient body are integral with said valve stem molded from a substantially rigid or semi-rigid plastic, and said resilient body molded from a substantially flexible, resilient plastic.

35. A fluid line connection assembly according to claim 30, wherein:

said valve member support includes a plurality of vane means extending substantially the entire length of said cylindrical chamber for centering said seating surface of said valve member against said first female luer.

* * * * *